(12) United States Patent
Ezerzer

(10) Patent No.: US 11,926,677 B2
(45) Date of Patent: Mar. 12, 2024

(54) PEPTIDES AND USES THEREOF FOR TREATING CANCER

(71) Applicant: SYMTHERA CANADA LTD., Ontario (CA)

(72) Inventor: Chai Ezerzer, Ness Ziona (IL)

(73) Assignee: SYMTHERA CANADA LTD., Ontario (CA)

( * ) Notice: Subject to any disclaimer, the term of this patent is extended or adjusted under 35 U.S.C. 154(b) by 0 days.

(21) Appl. No.: 17/084,765

(22) Filed: Oct. 30, 2020

(65) Prior Publication Data
US 2021/0188910 A1    Jun. 24, 2021

Related U.S. Application Data

(60) Provisional application No. 62/928,435, filed on Oct. 31, 2019.

(51) Int. Cl.
| | |
|---|---|
| C07K 7/06 | (2006.01) |
| A61K 45/06 | (2006.01) |
| A61P 35/00 | (2006.01) |
| C07K 7/08 | (2006.01) |
| C07K 14/00 | (2006.01) |
| A61K 38/00 | (2006.01) |

(52) U.S. Cl.
CPC ............... *C07K 7/06* (2013.01); *A61K 45/06* (2013.01); *A61P 35/00* (2018.01); *C07K 7/08* (2013.01); *C07K 14/001* (2013.01); *A61K 38/00* (2013.01)

(58) Field of Classification Search
None
See application file for complete search history.

(56) References Cited

U.S. PATENT DOCUMENTS

2013/0330335 A1    12/2013    Bremel et al.

FOREIGN PATENT DOCUMENTS

| WO | WO 2017/184590 | * | 10/2017 |
| WO | 2017/210600 A1 | | 12/2017 |
| WO | WO 2017/210600 | * | 12/2017 |

OTHER PUBLICATIONS

BLAST of SEQ ID No. 9 (retrieved from https://blast.ncbi.nlm.nih.gov/Blast.cgi on Feb. 17, 2022, 19 pages) (Year: 2022).*
WO 2017/210600 SEQ ID No. 3854 (retrieved from https://patentscope.wipo.int/search/en/detail.jsf?docId=WO2017210600&_cid=P10-KZR8YP-18331-1 on Feb. 17, 2022; document dated Dec. 7, 2017, 3 pages) (Year: 2017).*
Fry et al. ('Substrate specificity and cell cycle regulation of the Nek2 protein kinase, a potential human homolog of the mitotic regulator NIMA of Aspergillus nidulans' The Journal of Biological Chemistry v270(21) May 26, 1995 pp. 12899-12905) (Year: 1995).*
Schultz et al. ('Cell cycle-dependent expression of Nek2, a novel human protein kinase related to the NIMA mitotic regulator of Aspergillus nidulans' Cell Growth & Differentiation v5 Jun. 1994 pp. 625-635) (Year: 1994).*
'What is benzyl alcohol?' retrieved from https://www.harleystreetemporium.com/ingredient/benzyl-alcohol/ on Aug. 31, 2022, 5 pages (Year: 2022).*
Nutritional Outlook (retrieved from https://www.nutritionaloutlook.com/view/natural-preservatives-food-beverages-and-beauty-what-are-options on May 9, 2023, 2 pages) (Year: 2023).*
Lance A. Liotta et al., "*Principles of Molecular Cell Biology of Cancer: Cancer Metastasis*", 4th edition. Philadelphia, PA: JB Lippincott Co. (1993) pp. 134-149.
Albert-Laszlo Barabasi et al. "*Network biology: understanding the cell's functional organization*", Nature Reviews Genetics, vol. 5, Feb. 2004, pp. 101-114.
Ernesto Estrada "*Virtual identification of essential proteins within the protein interaction network of yeast*", Proteomics, 2006, vol. 6, pp. 35-40.
Miles A. Fabian et al. "*A small molecule-kinase interaction map for clinical kinase inhibitors*", Nature Biotechnology, vol. 34, No. 3, 2005, pp. 329-336.
Simon Franz "*Drug discovery: playing dirty*", Nature Publishing Group, 2005, 942-943.
Philip Gribbon et al. "*High-throughput drug discovery: what can we expect from HTS?*", Drug Discovery Today, 2005, vol. 10, No. 1, 6 pgs.
Tracy Hampton "*Promiscuous anticancer drugs that hit multiple targets may thwart resistance*", JAMA, 2004, vol. 292, No. 4, pp. 419-422.
Andrew L. Hopkins, "*Network biology illuminates our understanding of drug action*", Nature Biotechnology vol. 25, No. 10, (2007) pp. 1110-1111.
Sten Ohlson et al., "*Detection and characterization of weak affinity antibody antigen recognition with biomolecular interaction analysis*", Journal of Molecular Recognition, vol. 10, 1997, pp. 135-138.
Sten Ohlson "*Designing transient binding drugs: a new concept for drug discovery*" Drug Discovery Today, 2008, vol. 13, No. 9/10, pp. 433-439.
Christine A. Power "*Knock out models to dissect chemokine receptor function in vivo*", Journal of Immunological Methods, 273 (2003) pp. 73-82.

(Continued)

*Primary Examiner* — Ronald T Niebauer
(74) *Attorney, Agent, or Firm* — Pillsbury Winthrop Shaw Pittman, LLP

(57) ABSTRACT

Presented herein are cancer peptide agents and uses thereof for treating cancer and/or inhibiting metastasis. Also presented herein are methods of treating cancer, or inhibiting metastasis of cancer in a subject, comprising administering a therapeutically effective amount of a composition comprising one or more cancer peptide agents to the subject. Also presented herein is a method of treating a cancer in a subject, or inhibiting metastasis of a cancer in a subject that comprises administering a therapeutically effective amount of a composition comprising one or more cancer peptide agents, and administering a chemotherapy or chemotherapeutic agent.

17 Claims, 13 Drawing Sheets
Specification includes a Sequence Listing.

(56) References Cited

OTHER PUBLICATIONS

Bryan L. Roth et al. "*Magic shotguns versus magic bullets: selectively non-selective drugs for mood disorders and schizophrenia*" Nature Reviews Drug Discovery, vol. 3, 2004, pp. 353-259.

Heinz Ruffner et al., "*Human protein-protein interaction networks and the value for drug discovery*", Drug Discovery Today, vol. 12, No. 17/18, 2007, pp. 709-716.

Matthias K. Schwarz et al., "*New therapeutics that modulate chemokine networks*", Nature Reviews Drug Discovery, vol. 1, 2002, pp. 347-358.

Julian Vasilescu et al., "*Mapping protein-protein interactions by mass spectrometry*", Current Opinions in Biotechnology, 2006, vol. 17, pp. 394-399.

DT Wong, "Dual serotonin and noradrenaline uptake inhibitor class of antidepressants potential for greater efficacy or just hype?" Progress in Drug Research vol. 58, (2002) pp. 169-222.

Steven F. Altschul et al., "*Basic local alignment search tool*", J Mol. Biol., 1990, 215, pp. 403-410.

S. Karlin et al., "*Methods for assessing the statistical significance of molecular sequence features by using general scoring schemes*", Proc. Natl. Acad. Sci. USA 1990, vol. 87, pp. 2264-2268.

Amir Dembo et al., "*Limit distribution of maximal non-aligned two-sequence segmental score*", The Annals of Probability, 1994, vol. 22, No. 4, pp. 2022-2039.s.

P. Shannon et al., "*Cytoscape: a software environment for integrated models of biomolecular interaction networks*", Genome Research, No. 13, 2003, pp. 2498-2504.

Yassen Assenov et al., "*Computing topological parameters of biological networks*", Bioinformatics Vo. 24, No. 2, 2008, pp. 282-284.

Ann F. Chambers et al. "*Dissemination and growth of cancer cells in metastatic sites*", Nature Reviews, Cancer, vol. 2, Aug. 2002, pp. 563-572.

Isaiah J. Fidler, "*The pathogenesis of cancer metastasis: the 'seed and soil' hypothesis revisited*", Nature Reviews, Cancer, vol. 3, (2003), 6 pgs.

International Search Report and Written Opinion of International Searching Authority dated Jan. 13, 2021 issued in corresponding International Application No. PCT/IB2020/060207 (8 pgs.).

Ezerzer et al., "Chemokine receptor-derived peptides as multi-target drug leads for the treatment of inflammatory diseases", Peptides Jul. 1, 2009 (Jul. 1, 2009) vol. 30, No. 7, pp. 1296-1305.

\* cited by examiner

| Peptide Pattern | Protein 1 | Peptide 1 | Protein 2 | Peptide 2 |
|---|---|---|---|---|
| DVWSnGnnY | TTK | KSKISPKSDVWSLGCILYYMT | MELK | DVWSLGCILY |
| DnWSnGCnnY | PLK1 | DVWSIGCIMYTLLVGKPPFET | TTK | DVWSIGCIMY |
| DnWSnGnnLY | MELK | GKYDVPKWLSPSSILLLQQML | TTK | DVWSMGILLY |
| KSDnWSLGCnLY | TTK | KSKISPKSDVWSLGCILYYMT | NEK2 | KSDVWSLGCILY |

| Peptide 2 | Protein 3 | Peptide 3 |
|---|---|---|
| GKYDVPKWLSPSSILLQQML DVWSMGILLY | PLK1 | DVWSIGCIMYTLLVGKPPFET DVWSIGCIMY |
| KSKISPKSDVWSLGCILYYMT DVWSLGCILY | NEK2 | NEKSDIWSLGCLLYELCALMP DIWSLGCLLY |
| KSKISPKSDVWSLGCILYYMT DVWSLGCILY | NEK2 | NEKSDIWSLGCLLYELCALMP DIWSLGCLLY |
| NEKSDIWSLGCLLYELCALMP KSDIWSLGCLLY | | |

| Internal Name | Peptide Pattern | | | | | | | | | Source |
|---|---|---|---|---|---|---|---|---|---|---|
| IR5-01 | D | I | W | S | L | G | C | L | L | Y | Nek2A |
| IR5-02 | D | V | W | S | M | G | I | L | L | Y | MELK |
| IR13-01 | D | V | W | S | L | G | C | I | L | Y | TTK |
| IR13-02 | D | V | W | S | I | G | C | I | L | M | Y | PLK1 |
| | D | V | W | S | | G | C | L | L | Y |
| | | | | | | | | I | | |

FIG. 2B

| Internal Name | Peptide Pattern | Name | % CS |
|---|---|---|---|
| IR5-01 | DIWSLGCLLY | DLGP5 | 0.8 |
| IR13-01 | DVWSLGCILY | RB | 0.7 |
| | DVWSLGCILY | ESPL1 | 0.7 |
| | DVWSLGCILY | MELK | 0.7 |
| | DVWSLGCILY | MELK | 0.7 |
| | DVWSLGCILY | RBL1 | 0.7 |
| | DVWSLGCILY | CCNB2 | 0.7 |
| | DVWSLGCILY | DLGP5 | 0.7 |
| | DVWSLGCILY | RB | 0.7 |
| | DVWSLGCILY | ESPL1 | 0.7 |
| | DVWSLGCILY | MELK | 0.7 |
| | DVWSLGCILY | MELK | 0.7 |
| | DVWSLGCILY | RBL1 | 0.7 |
| | DVWSLGCILY | CCNB2 | 0.7 |
| | DVWSLGCILY | DLGP5 | 0.7 |
| IR5-01 | DIWSLGCLLY | ESPL1 | 0.7 |
| | DIWSLGCLLY | FOXM1 | 0.7 |
| | DIWSLGCLLY | CENPE | 0.7 |
| | DIWSLGCLLY | TF65 | 0.7 |
| | DIWSLGCLLY | DLGP5 | 0.7 |
| | DIWSLGCLLY | CCNA2 | 0.7 |
| IR13-02 | DVWSIGCIMY | NEK2 | 0.7 |
| IR5-02 | DVWSMGILLY | CENPF | 0.7 |
| | DVWSMGILLY | FOXM1 | 0.7 |
| | DVWSMGILLY | CENPF | 0.7 |
| | DVWSMGILLY | FOXM1 | 0.7 |
| IR13-02 | DVWSIGCIMY | TTK | 0.6 |
| | DVWSIGCIMY | ESPL1 | 0.6 |
| | DVWSIGCIMY | ESPL1 | 0.6 |
| | DVWSIGCIMY | KIF2C | 0.6 |
| | DVWSIGCIMY | CCNB2 | 0.6 |
| | DVWSIGCIMY | CCNB2 | 0.6 |
| | DVWSIGCIMY | CCNB2 | 0.6 |
| | DVWSIGCIMY | ATAD2 | 0.6 |
| | DVWSIGCIMY | ATAD2 | 0.6 |
| | DVWSIGCIMY | CENPE | 0.6 |
| IR13-01 | DVWSLGCILY | TOP2A | 0.6 |

FIG. 3

| Group | | weight [mg] | mice # | big | small | Total |
|---|---|---|---|---|---|---|
| group No. 5 | 1 | 210 | 2341 | 2 | 1 | 3 |
| IR5 | 2 | 190 | 2342 | 1 | 0 | 1 |
| IV[200ug] | 3 | 200 | 2343 | 0 | 0 | 0 |
| | 4 | 170 | 2344 | 3 | 3 | 6 |
| | 5 | 170 | 2345 | 2 | 0 | 2 |
| | 6 | 180 | 2346 | 1 | 1 | 2 |
| | 7 | 190 | 2347 | 2 | 0 | 2 |
| | 8 | 200 | 2348 | 0 | 0 | 0 |
| | 9 | 180 | 2349 | 3 | 1 | 4 |
| | 10 | 210 | 2350 | 2 | 0 | 2 |
| group No. 6 | 1 | 320 | 2351 | 7 | 10 | 17 |
| 1% DMSO | 2 | 270 | 2352 | 5 | 8 | 13 |
| IV[200ug] | 3 | 420 | 2353 | 9 | 12 | 21 |
| | 4 | 400 | 2354 | 7 | 8 | 15 |
| | 5 | 180 | 2355 | 2 | 3 | 5 |
| | 6 | 210 | 2356 | 6 | 3 | 9 |
| | 7 | 300 | 2357 | 5 | 6 | 11 |
| | 8 | 490 | 2358 | 16 | 8 | 24 |
| | 9 | 280 | 2359 | 8 | 5 | 13 |
| | 10 | 210 | 2360 | 4 | 4 | 8 |

FIG. 4

|        | non-treated | dmso 0.5% | 100 ug IR5 | 200 ug IR5 |
|--------|-------------|-----------|------------|------------|
| 1st q  | 5           | 5         | 0          | 0          |
| min    | 2           | 0         | 0          | 0          |
| median | 8           | 8         | 1          | 0          |
| max    | 26          | 40        | 3          | 5          |
| 3rd q  | 13          | 13        | 2          | 1          |

Mann-Whitney U
p value calculated from Z-score
100 ug IR5 vs DMSO 0.5%: The P-Value is < 0.00001
200 ug IR5 vs DMSO 0.5%: The P-Value is 1.1E-05.
DMSO vs non-treated: The *p*-value is .48006. The result is *not* significant at *p* < .01.

| mouse # | 1 | 2 | 3 | 4 | 5 | 6 | 7 | 8 | 9 | 10 | 11 | 12 | 13 | 14 | 15 | 16 | 17 |
|---|---|---|---|---|---|---|---|---|---|---|---|---|---|---|---|---|---|
| Non-treated | 2 | 3 | 4 | 4 | 5 | 6 | 7 | 8 | 8 | 8 | 10 | 10 | 13 | 16 | 17 | 18 | 26 |
| DMSO 0.5% | 0 | 3 | 4 | 5 | 5 | 6 | 6 | 7 | 8 | 8 | 9 | 12 | 15 | 27 | 32 | 40 | |
| 100 ug | 0 | 0 | 0 | 0 | 0 | 0 | 0 | 0 | 1 | 1 | 2 | 2 | 2 | 2 | 3 | 3 | |
| 200 ug | 0 | 0 | 0 | 0 | 0 | 0 | 0 | 0 | 0 | 1 | 1 | 1 | 1 | 2 | 3 | 4 | 5 |

FIG. 7

SEQUENCE LISTING

```
<160> NUMBER OF SEQ ID NOS: 36

<210> SEQ ID NO 1
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Any amino acid
<220> FEATURE:
<221> NAME/KEY: MOD_RES
<222> LOCATION: (7)..(9)
<223> OTHER INFORMATION: Any amino acid

<400> SEQUENCE: 1

Asp Val Trp Ser Xaa Gly Xaa Xaa Xaa Tyr
1               5                   10

<210> SEQ ID NO 2
<211> LENGTH: 10
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (5)..(5)
<223> OTHER INFORMATION: Any amino acid
<220> FEATURE:
<221> NAME/KEY: MOD_RES
<222> LOCATION: (8)..(9)
<223> OTHER INFORMATION: Any amino acid

<400> SEQUENCE: 2

Asp Xaa Trp Ser Xaa Gly Cys Xaa Xaa Tyr
1               5                   10

<210> SEQ ID NO 3
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (5)..(5)
<223> OTHER INFORMATION: Any amino acid
<220> FEATURE:
<221> NAME/KEY: MOD_RES
<222> LOCATION: (7)..(8)
<223> OTHER INFORMATION: Any amino acid

<400> SEQUENCE: 3

Asp Xaa Trp Ser Xaa Gly Xaa Xaa Leu Tyr
1               5                   10

<210> SEQ ID NO 4
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Any amino acid
<220> FEATURE:
<221> NAME/KEY: MOD_RES
<222> LOCATION: (10)..(10)
<223> OTHER INFORMATION: Any amino acid

<400> SEQUENCE: 4

Lys Ser Asp Xaa Trp Ser Leu Gly Cys Xaa Leu Tyr
1               5                   10

<210> SEQ ID NO 5
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<221> NAME/KEY: MOD_RES
<222> LOCATION: (2)..(2)
<223> OTHER INFORMATION: Ile or Val
<220> FEATURE:
<221> NAME/KEY: MOD_RES
<222> LOCATION: (5)..(5)
<223> OTHER INFORMATION: Leu, Met or Ile
<220> FEATURE:
<221> NAME/KEY: MOD_RES
<222> LOCATION: (7)..(7)
<223> OTHER INFORMATION: Cys or Ile
<220> FEATURE:
<221> NAME/KEY: MOD_RES
<222> LOCATION: (8)..(8)
<223> OTHER INFORMATION: Leu or Ile
<220> FEATURE:
<221> NAME/KEY: MOD_RES
<222> LOCATION: (9)..(9)
<223> OTHER INFORMATION: Leu or Met

<400> SEQUENCE: 5

Asp Xaa Trp Ser Xaa Gly Xaa Xaa Xaa Tyr
1               5                   10

<210> SEQ ID NO 6
<211> LENGTH: 10
<212> TYPE: PRT
<213> ORGANISM: Homo sapiens

<400> SEQUENCE: 6

Asp Val Trp Ser Leu Gly Cys Ile Leu Tyr
1               5                   10

<210> SEQ ID NO 7
<211> LENGTH: 10
<212> TYPE: PRT
<213> ORGANISM: Homo sapiens

<400> SEQUENCE: 7

Asp Val Trp Ser Ile Gly Cys Ile Met Tyr
1               5                   10

<210> SEQ ID NO 8
<211> LENGTH: 10
<212> TYPE: PRT
<213> ORGANISM: Homo sapiens

<400> SEQUENCE: 8

Asp Val Trp Ser Met Gly Ile Leu Leu Tyr
1               5                   10

<210> SEQ ID NO 9
<211> LENGTH: 10
<212> TYPE: PRT
<213> ORGANISM: Homo sapiens

<400> SEQUENCE: 9

Asp Ile Trp Ser Leu Gly Cys Leu Leu Tyr
1               5                   10

<210> SEQ ID NO 10
<211> LENGTH: 12
<212> TYPE: PRT
<213> ORGANISM: Homo sapiens

<400> SEQUENCE: 10

Lys Ser Asp Val Trp Ser Leu Gly Cys Ile Leu Tyr
```

```
                              1               5                   10

<210> SEQ ID NO 11
<211> LENGTH: 21
<212> TYPE: PRT
<213> ORGANISM: Homo sapiens

<400> SEQUENCE: 11

Lys Ser Lys Ile Ser Pro Lys Ser Asp Val Trp Ser Leu Gly Cys Ile
1               5                   10                  15

Leu Tyr Tyr Met Thr
            20

<210> SEQ ID NO 12
<211> LENGTH: 21
<212> TYPE: PRT
<213> ORGANISM: Homo sapiens

<400> SEQUENCE: 12

Asp Val Trp Ser Ile Gly Cys Ile Met Tyr Thr Leu Leu Val Gly Lys
1               5                   10                  15

Pro Pro Phe Glu Thr
            20

<210> SEQ ID NO 13
<211> LENGTH: 21
<212> TYPE: PRT
<213> ORGANISM: Homo sapiens

<400> SEQUENCE: 13

Gly Lys Tyr Asp Val Pro Lys Trp Leu Ser Pro Ser Ser Ile Leu Leu
1               5                   10                  15

Leu Gln Gln Met Leu
            20

<210> SEQ ID NO 14
<211> LENGTH: 10
<212> TYPE: PRT
<213> ORGANISM: Homo sapiens

<400> SEQUENCE: 14

Asp Val Trp Ser Leu Gly Cys Leu Leu Tyr
1               5                   10

<210> SEQ ID NO 15
<211> LENGTH: 21
<212> TYPE: PRT
<213> ORGANISM: Homo sapiens

<400> SEQUENCE: 15

Asn Glu Lys Ser Asp Ile Trp Ser Leu Gly Cys Leu Leu Tyr Glu Leu
1               5                   10                  15

Cys Ala Leu Met Pro
            20

<210> SEQ ID NO 16
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
```

```
<222> LOCATION: (2)..(2)
<223> OTHER INFORMATION: Ile, Val or Leu
<220> FEATURE:
<221> NAME/KEY: MOD_RES
<222> LOCATION: (5)..(5)
<223> OTHER INFORMATION: Ile, Val, Leu or Met
<220> FEATURE:
<221> NAME/KEY: MOD_RES
<222> LOCATION: (7)..(7)
<223> OTHER INFORMATION: Cys, Ile, Val or Leu
<220> FEATURE:
<221> NAME/KEY: MOD_RES
<222> LOCATION: (8)..(8)
<223> OTHER INFORMATION: Ile, Val or Leu
<220> FEATURE:
<221> NAME/KEY: MOD_RES
<222> LOCATION: (9)..(9)
<223> OTHER INFORMATION: Ile, Val, Leu or Met

<400> SEQUENCE: 16

Asp Xaa Trp Ser Xaa Gly Xaa Xaa Xaa Tyr
1               5                   10

<210> SEQ ID NO 17
<211> LENGTH: 16
<212> TYPE: PRT
<213> ORGANISM: Homo sapiens

<400> SEQUENCE: 17

Phe Ala Tyr Gly Gln Thr Ala Ser Gly Lys Thr Tyr Thr Met Met Gly
1               5                   10                  15

<210> SEQ ID NO 18
<211> LENGTH: 13
<212> TYPE: PRT
<213> ORGANISM: Homo sapiens

<400> SEQUENCE: 18

Leu Val Asp Leu Ala Gly Asn Glu Arg Gly Ala Asp Thr
1               5                   10

<210> SEQ ID NO 19
<211> LENGTH: 10
<212> TYPE: PRT
<213> ORGANISM: Homo sapiens

<400> SEQUENCE: 19

Glu Ala Gln Lys Lys Pro Ala Glu Ser Gln
1               5                   10

<210> SEQ ID NO 20
<211> LENGTH: 16
<212> TYPE: PRT
<213> ORGANISM: Homo sapiens

<400> SEQUENCE: 20

Phe Ala Tyr Gly Gln Thr Gly Ser Gly Lys Ser Tyr Thr Met Met Gly
1               5                   10                  15

<210> SEQ ID NO 21
<211> LENGTH: 17
<212> TYPE: PRT
<213> ORGANISM: Homo sapiens

<400> SEQUENCE: 21

Leu Gln Leu Val Gly Ile Thr Ala Leu Leu Leu Ala Ser Lys Tyr Glu
1               5                   10                  15
```

Glu

<210> SEQ ID NO 22
<211> LENGTH: 10
<212> TYPE: PRT
<213> ORGANISM: Homo sapiens

<400> SEQUENCE: 22

Glu Leu Gln Lys Lys Gln Val Glu Leu Gln
1               5                   10

<210> SEQ ID NO 23
<211> LENGTH: 10
<212> TYPE: PRT
<213> ORGANISM: Homo sapiens

<400> SEQUENCE: 23

Lys Lys Ile Lys Glu Leu Gln Lys Gly Glu
1               5                   10

<210> SEQ ID NO 24
<211> LENGTH: 16
<212> TYPE: PRT
<213> ORGANISM: Homo sapiens

<400> SEQUENCE: 24

Phe Ala Tyr Gly Gln Thr Gly Ser Gly Lys Thr Phe Thr Met Glu Gly
1               5                   10                  15

<210> SEQ ID NO 25
<211> LENGTH: 13
<212> TYPE: PRT
<213> ORGANISM: Homo sapiens

<400> SEQUENCE: 25

Leu Val Asp Leu Ala Gly Ser Glu Arg Thr Asn Arg Thr
1               5                   10

<210> SEQ ID NO 26
<211> LENGTH: 12
<212> TYPE: PRT
<213> ORGANISM: Homo sapiens

<400> SEQUENCE: 26

His Arg Asp Leu Lys Pro Gln Asn Leu Leu Ile Asp
1               5                   10

<210> SEQ ID NO 27
<211> LENGTH: 17
<212> TYPE: PRT
<213> ORGANISM: Homo sapiens

<400> SEQUENCE: 27

Leu Gln Leu Val Gly Thr Ala Ala Met Leu Leu Ala Ser Lys Phe Glu
1               5                   10                  15

Glu

<210> SEQ ID NO 28
<211> LENGTH: 17
<212> TYPE: PRT
<213> ORGANISM: Homo sapiens

<400> SEQUENCE: 28

Leu Gln Leu Val Gly Val Thr Ala Met Phe Ile Ala Ser Lys Tyr Glu

Glu

<210> SEQ ID NO 29
<211> LENGTH: 11
<212> TYPE: PRT
<213> ORGANISM: Homo sapiens

<400> SEQUENCE: 29

Leu Phe Tyr Gly Pro Pro Gly Thr Gly Lys Thr
1               5                   10

<210> SEQ ID NO 30
<211> LENGTH: 12
<212> TYPE: PRT
<213> ORGANISM: Homo sapiens

<400> SEQUENCE: 30

Lys Ser Asp Ile Trp Ser Leu Gly Cys Leu Leu Tyr
1               5                   10

<210> SEQ ID NO 31
<211> LENGTH: 10
<212> TYPE: PRT
<213> ORGANISM: Homo sapiens

<400> SEQUENCE: 31

Lys Lys Ile Gln Glu Leu Gln Lys Lys Glu
1               5                   10

<210> SEQ ID NO 32
<211> LENGTH: 9
<212> TYPE: PRT
<213> ORGANISM: Homo sapiens

<400> SEQUENCE: 32

Lys Lys Pro Ala Glu Ser Gln Lys Ile
1               5

<210> SEQ ID NO 33
<211> LENGTH: 13
<212> TYPE: PRT
<213> ORGANISM: Homo sapiens

<400> SEQUENCE: 33

Leu Val Asp Leu Ala Gly Ser Glu Arg Ala Ala Gln Thr
1               5                   10

<210> SEQ ID NO 34
<211> LENGTH: 16
<212> TYPE: PRT
<213> ORGANISM: Homo sapiens

<400> SEQUENCE: 34

Phe Thr Tyr Gly Val Thr Gly Ser Gly Lys Thr His Thr Met Thr Gly
1               5                   10                  15

<210> SEQ ID NO 35
<211> LENGTH: 22
<212> TYPE: PRT
<213> ORGANISM: Homo sapiens

<400> SEQUENCE: 35

Gly Gly Lys Ala Thr Cys Phe Ala Tyr Gly Gln Thr Gly Ser Gly Lys

```
1               5               10              15
Thr His Thr Met Gly Gly
            20

<210> SEQ ID NO 36
<211> LENGTH: 22
<212> TYPE: PRT
<213> ORGANISM: Homo sapiens

<400> SEQUENCE: 36

Gly Phe Asn Thr Cys Leu Phe Ala Tyr Gly Gln Thr Gly Ser Gly Lys
1               5                   10                  15

Ser Tyr Thr Met Met Gly
            20
```

PEPTIDES AND USES THEREOF FOR TREATING CANCER

CROSS-REFERENCE TO RELATED APPLICATIONS

This application claims priority to U.S. Provisional Patent Application No. 62/928,435, filed Oct. 31, 2019, the subject matter of which is incorporated herein by reference in its entirety.

SEQUENCE LISTING

The instant application contains a Sequence Listing which has been submitted electronically in ASCII format and is hereby incorporated by reference in its entirety. Said ASCII copy, created on Dec. 7, 2020, is named 035159-0515836_SL.txt and is 8,582 bytes in size.

FIELD OF THE INVENTION

Embodiments relate to cancer peptide agents, and uses thereof.

INTRODUCTION

Metastasis is the spread of a cancer from one organ or location in a body to another organ or location in the body. Metastasis of cancer is an extremely complex process involving a series of cellular changes that result in the ability of a cancer cell to successfully colonize a secondary site. The process of metastasis includes a cascade of events often including dissemination of a cancer cell from a primary tumor, migration of cancer cell through the basement membrane, mobilization of a cancer cell into the circulatory system, invasion of a cancer cell into a secondary site, and proliferation of a cancer cell at the secondary site (MacDonald IC, 2002). Metastasis is of great importance to the clinical management of cancer since the majority of cancer mortality is associated with metastatic cancers.

A majority of cancer patients die due to tumor metastasis, often because a cancer metastasizes before it is diagnosed. There are no drugs presently available that specifically inhibit the metastasis of cancer cells. Presented herein are novel peptides and uses thereof to inhibit metastasis and treat cancer.

SUMMARY

In some aspects, presented herein are cancer peptide agents and/or pharmaceutical composition comprising one or more cancer peptide agents. A pharmaceutical composition may comprise one or more pharmaceutically acceptable excipients or carriers. In some embodiments, a cancer peptide agent comprises an amino acid sequence selected from the amino acid sequence of DVWSXGXXXY (SEQ ID NO:1), DXWSXGCXXY (SEQ ID NO:2), DXWSXGXXLY (SEQ ID NO:3) and KSDXWSLGCXLY (SEQ ID NO:4), where X is any amino acid. In certain embodiments, a cancer peptide agent comprises the amino acid sequence of D(I/V)WS(L/M/I)G(C/I)(L/I)(L/M)Y (SEQ ID NO:5). In certain embodiments, a cancer peptide agent comprises the amino acid sequence of DVWSLGCILY (SEQ ID NO:6), DVWSIGCIMY (SEQ ID NO:7), DVWSMGILLY (SEQ ID NO:8), DIWSLGCLLY (SEQ ID NO:9), and DVWSLGCLLY (SEQ ID NO:14). In certain embodiments, a cancer peptide agent comprises the amino acid sequence of KSDVWSLGCILY (SEQ ID NO:10), KSKISPKSDVWSLGCILYYMT (SEQ ID NO:11), DVWSIGCIMYTLLVGKPPFET (SEQ ID NO:12), GKYDVPKWLSPSSILLLQQML (SEQ ID NO:13), and NEKSDIWSLGCLLYELCALMP (SEQ ID NO:15). In some embodiments, a cancer peptide agent has a length of 50 amino acids or less. In some embodiments, a cancer peptide agent has a length of 15 amino acids or less.

In some aspects, presented herein is a method of treating cancer in a subject in need thereof comprising administering a therapeutically effective amount of a composition comprising one or more cancer peptide agents to the subject. In some aspects, presented herein is a method of inhibiting metastasis of a cancer in a subject comprising administering a therapeutically effective amount of a composition comprising one or more cancer peptide agents to the subject. In certain embodiments, a cancer is selected from a carcinoma, adenocarcinoma, melanoma, neural neoplasia, sarcoma, lymphomas, myeloma, and leukemia. In some embodiments a method of treating a cancer in a subject, or inhibiting metastasis of a cancer in a subject further comprises administering a chemotherapy or chemotherapeutic agent.

Certain aspects of the technology are described further in the following description, examples, claims and drawings.

BRIEF DESCRIPTION OF THE DRAWINGS

The drawings illustrate embodiments of the technology and are not limiting. For clarity and ease of illustration, the drawings are not made to scale and, in some instances, various aspects may be shown exaggerated or enlarged to facilitate an understanding of particular embodiments.

FIG. 1A-FIG. 1C show an in silico-array analysis of Cancer Metastasis Binding Peptides (CMBPs) and certain Cancer Metastasis-Associated Proteins (CMAPs) to determine their protein-peptide binding specificity and relative binding strengths. FIG. 1A-1C disclose SEQ ID NOS 17-21, 9, 22-23, 8, 24-33, 7, 34, 6, 10, and 35-36, respectively, in order of appearance.

FIGS. 2A.I, 2A.II and 2B Hidden Patterns. FIGS. 2A.I and 2A.II show the results of an in silico network analysis of CMAPs found in table 1 identifying several cancer binding agents. The motifs: [DVWSXGXXXY (SEQ ID NO: 1)], [DXWSXGCXXY (SEQ ID NO: 2)], [DXWSXGXXLY (SEQ ID NO: 3)], and [KSDXWSLGCXLY (SEQ ID NO: 4)], where "X" is any amino acid, were found to connect certain clusters of CMAPs. FIGS. 2A.I and 2A.II disclose the sequences in the "Peptide 1" column as SEQ ID NOS 11, 6, 12, 7, 13, 8, 11 and 10, the sequences in the "Peptide 2" column as SEQ ID NOS 13, 8, 11, 6, 11, 6, 15 and 30, and the sequences in the "Peptide 3" column as SEQ ID NOS 12, 7, 15, 9, 15 and 9, all respectively, in order of appearance. FIG. 2B shows cancer peptide agents IR5-01, IR5-02, IR13-01, IR13-02 and two additional cancer peptide agents. FIG. 2B discloses SEQ ID NOS 9, 8, 6-7, 14 and 6, respectively, in order of appearance.

FIG. 3—Sequence-Sharing Hidden Patterns network of potential interaction with the different CMAPs. FIG. 3 shows probable sets of interactions by calculating the complementary percentages between the CMBPs and the library of all the CMAPs. FIG. 3 discloses "DVWSLGCILY", "DVWSIGCIMY", "DVWSMGILLY", and "DIWSLGCLLY" as SEQ ID NOS 6-9, respectively.

FIG. 4—Source data Weight, lung nodule size, and the total of lung nodules per mouse. FIG. 4 shows the total number of lung tumors (nodules) and relative size of nodules identified in mice treated with cancer peptide agent IR5-01 (mouse #2341-2350; Group 5) or mice treated with control DMSO (mouse #2351-2360; Group 6). Details of the experiment are provided in Example 2. Pulmonary metastatic foci were measured and counted 3-weeks after IV (intravenous injection) of B16F10 cells.

FIG. 7 shows raw data of the mice shown and described in FIG. 6A and FIG. 6B. Numbers for non-treated or treated mice indicate the number of lung nodules per mouse.

DETAILED DESCRIPTION

Figure 1A:
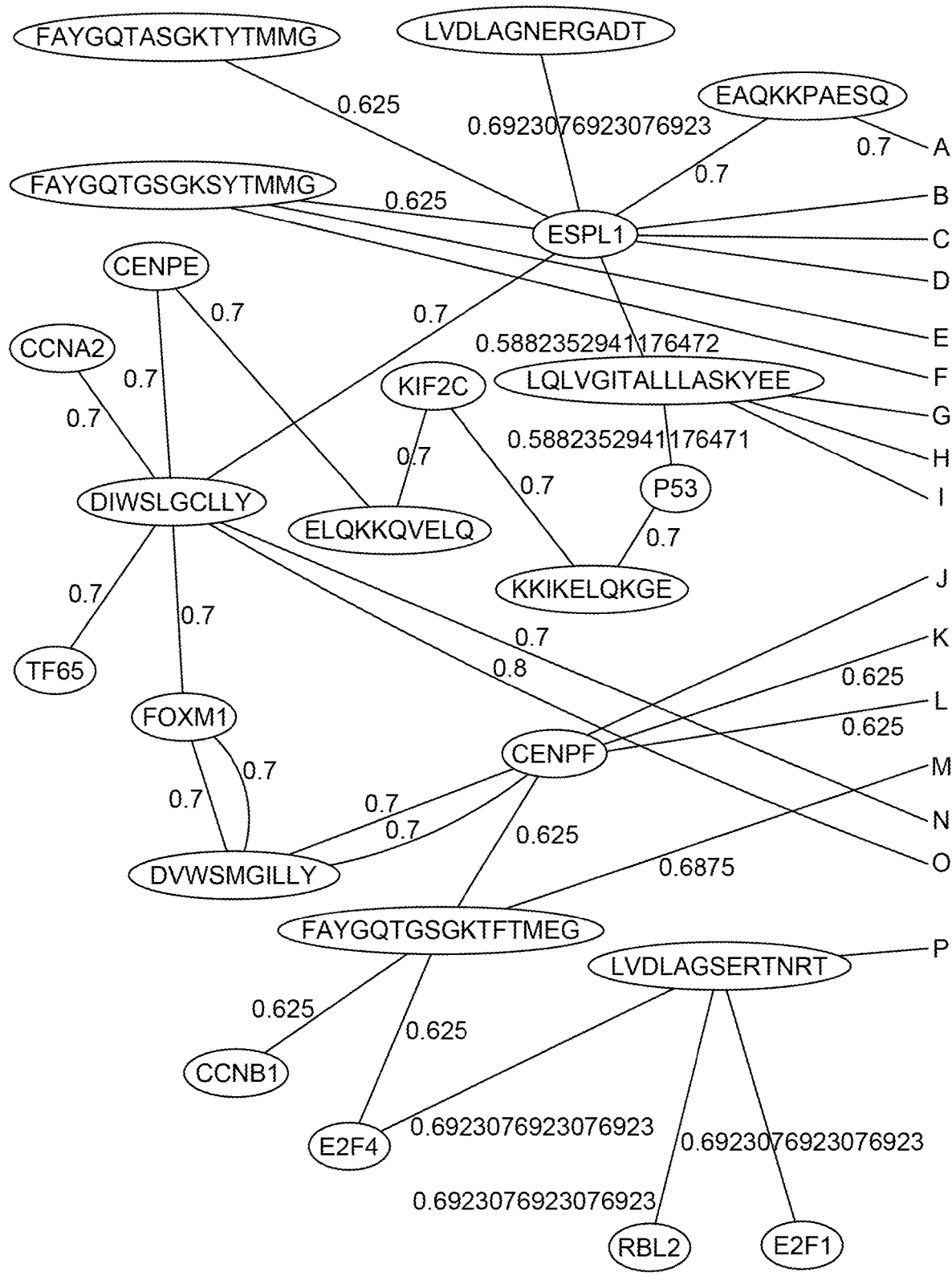
FIG. 1A-FIG. 1C—Sequence Sharing Network of different hidden patterns.

Presented herein are cancer peptide agents and uses thereof, for example, for treating a subject having, or suspected of having a cancer. In some embodiments a cancer peptide agent is a small peptide comprising an amino acid sequence motif that is shared among a networked cluster of cancer metastasis associated proteins (CMAPs). The novel in silico process used to identify and design the cancer peptide agents described herein is outlined in Example 1. Without being limited to theory, the cancer peptide agents described herein are thought to inhibit the function of cancer cell proteins and/or protein-protein interactions that are required for a cancer cell to metastasize. Accordingly, in certain embodiments, the cancer peptide agents described herein are used to inhibit, suppress, ameliorate, or reduce metastasis of a cancer in a subject.

Subjects

The term "subject" refers to animals, typically mammalian animals. In some embodiments a subject is a mammal. Any suitable mammal can be treated by a method described herein. Non-limiting examples of mammals include humans, non-human primates (e.g., apes, gibbons, chimpanzees, orangutans, monkeys, macaques, and the like), domestic animals (e.g., dogs and cats), farm animals (e.g., horses, cows, goats, sheep, pigs) and experimental animals (e.g., mouse, rat, rabbit, guinea pig). In some embodiments a subject is a primate. In some embodiments a subject is a human. A mammal can be any age or at any stage of development (e.g., an adult, teen, child, infant, or a mammal in utero). A mammal can be male or female. In certain embodiments a mammal can be an animal disease model, for example, animal models used for the study of cancer.

In certain embodiments a subject has or is suspected of having a cancer. In certain embodiments a subject is at risk of developing a cancer. Subjects at risk of developing a cancer can be subjects in high risk groups who can be identified by a medical professional. Non-limiting examples of subjects at risk of cancer include chronic smokers, overweight individuals, human subjects over the age of 60, subjects with a family history of cancer, subjects having certain gene mutations that are associated with certain cancers, subjects infected with, or previously infected with certain viruses associated with the development of certain cancers, subjects exposed to known carcinogens, subjects exposed to excessive radiation (e.g., UV radiation, alpha, beta, or gamma radiation), subjects having chronic inflammation, the like, or combinations thereof. In some embodiments a subject or mammal is "at risk" of cancer metastasis. Certain cancers are known to be metastatic or have a high probability of metastasis depending on the cancer type, stage, tissue or origin, and/or age, sex or health condition of a subject. A subject at risk can be readily identified by a medical professional (e.g., a doctor, or an oncologists).

Cancer Peptide Agents

Presented herein, in certain embodiments, are methods of treating a subject having, or suspected of having a cancer, which methods comprise administering to a subject in need thereof, a therapeutically effective amount of one or more cancer peptide agents, or a therapeutically effective amount of a pharmaceutical composition comprising one or more cancer peptide agents.

Figure 1B:
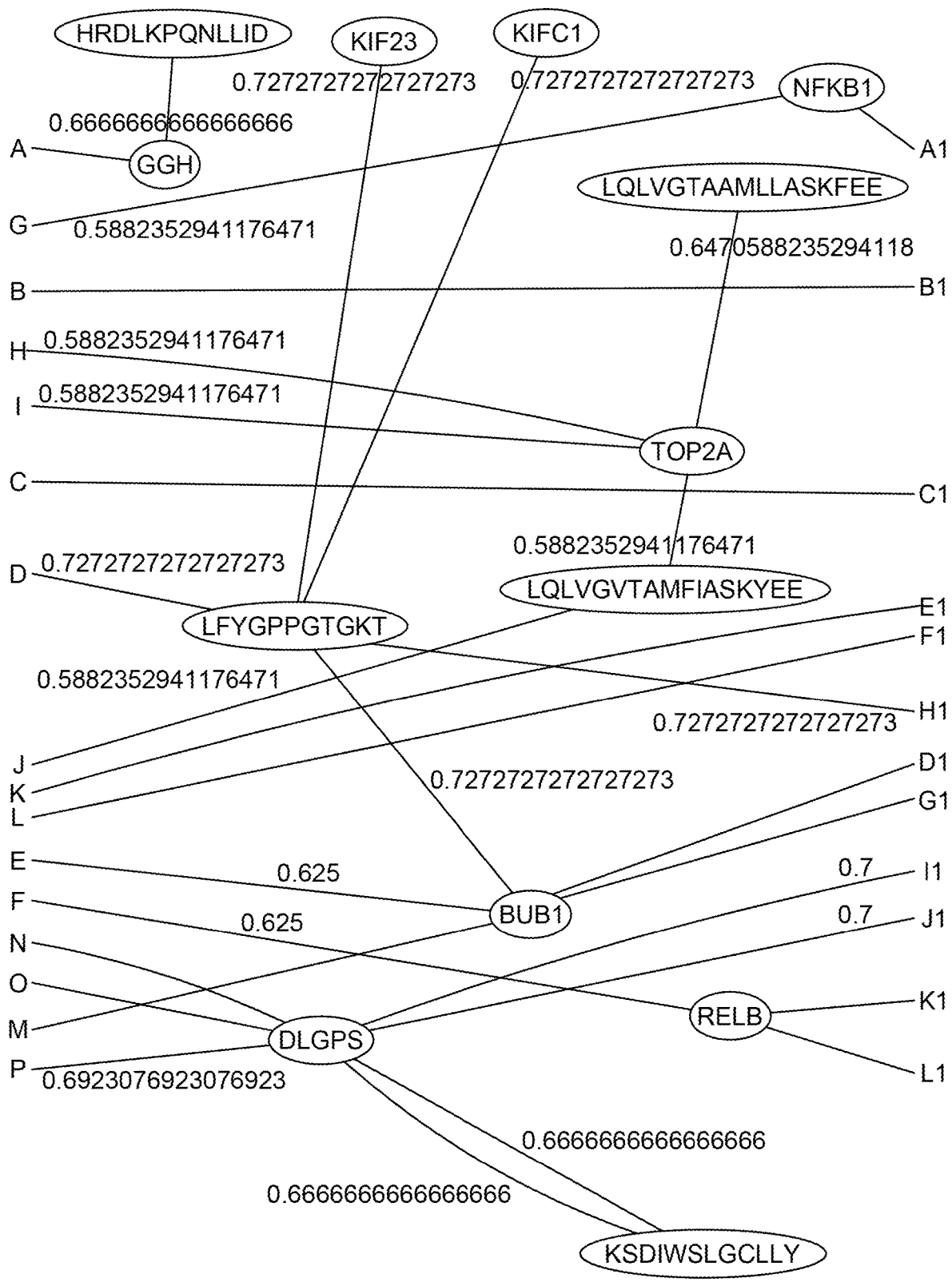
Figure 1C:
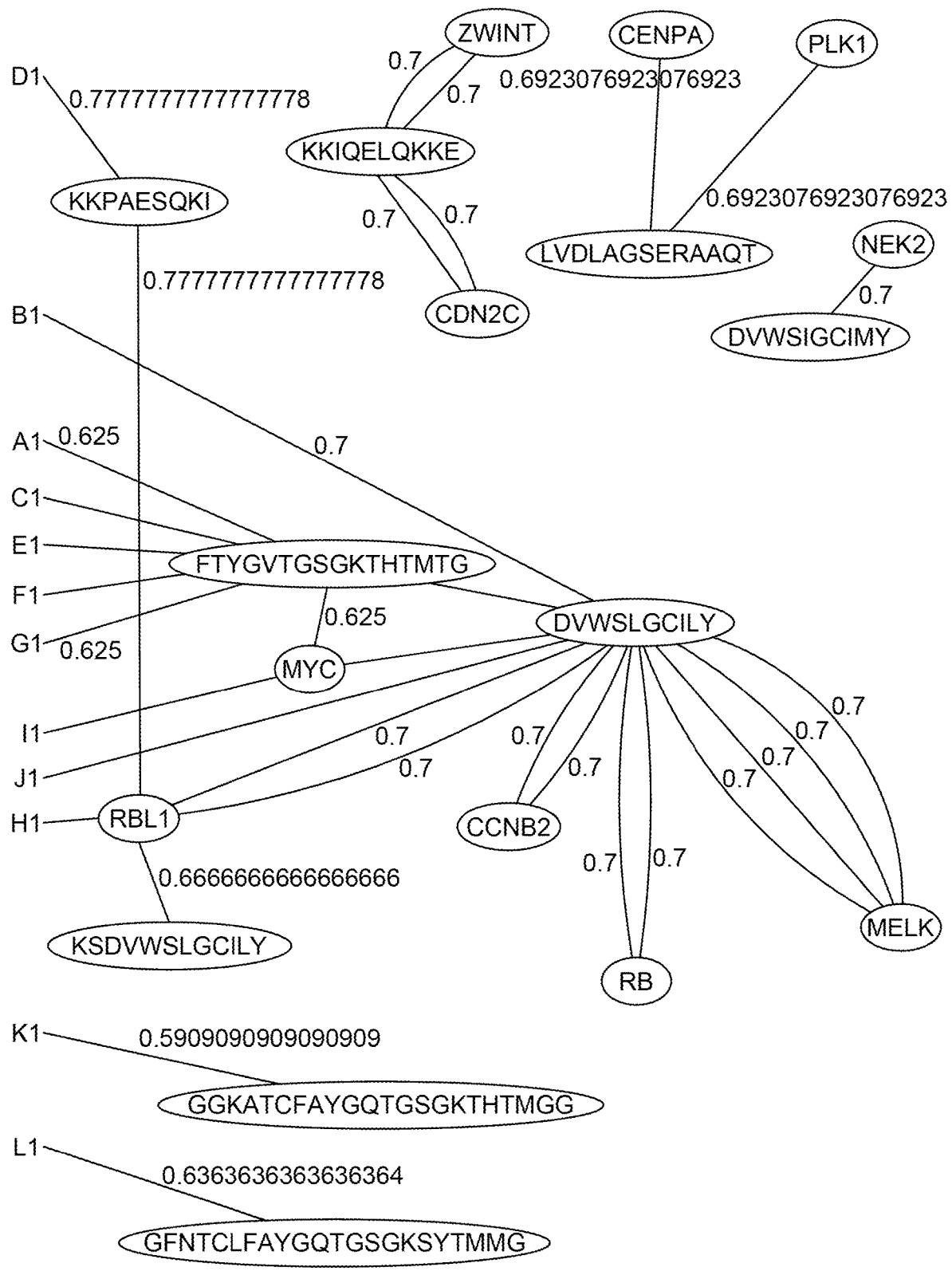
Figure 5:
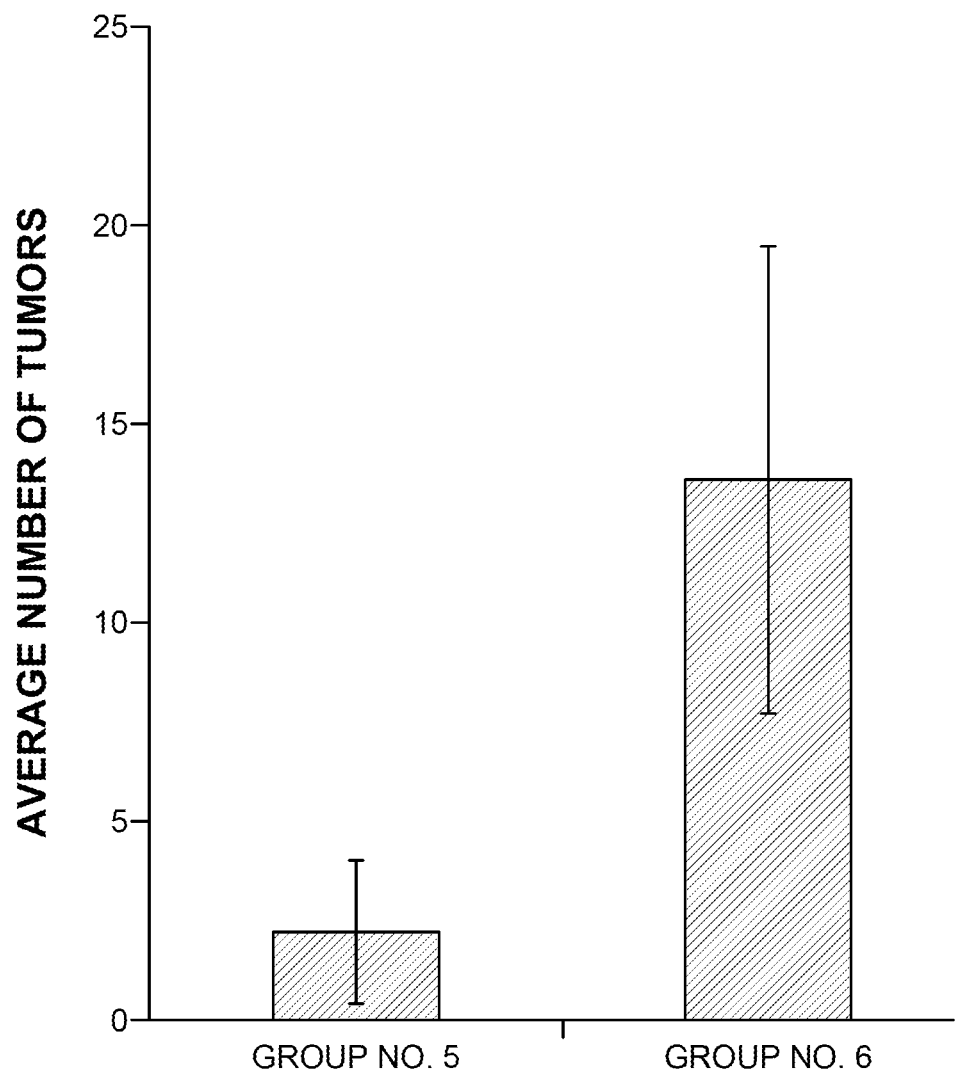
FIG. 5 shows a histogram showing the average number of pulmonary B16F10 metastatic tumors per group.
Figures 6A, 6B:
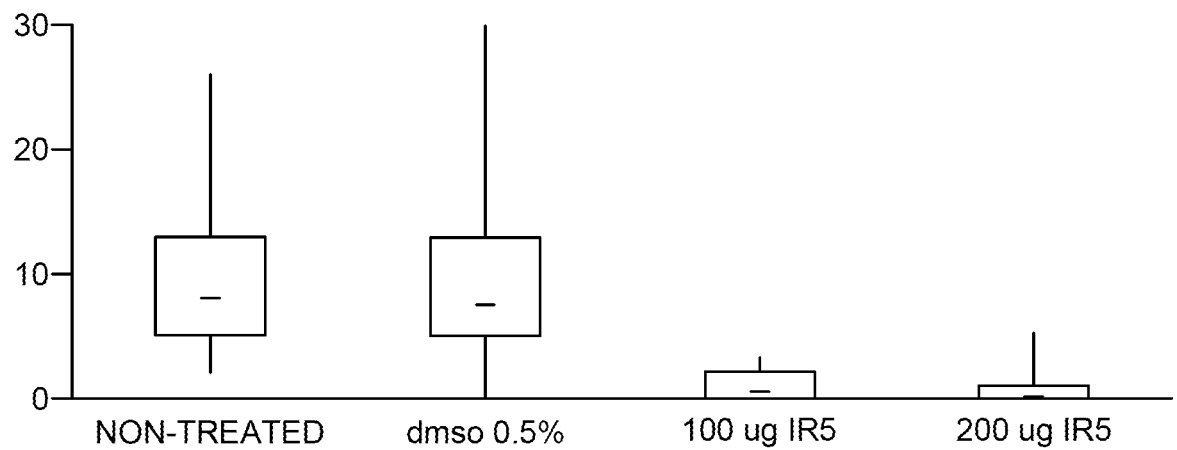
FIGS. 6A and 6B shows the average number of metastatic tumor nodules (FIG. 6B, y-axis) of C57B1 mice injected with 200,000 B16 cells and either not treated, treated with DMSO, treated with 100 μg of IR5-01, or treated with 200 μg of IR5-01. Lungs were harvested at day 28. Treatment was administered daily after injection of B16 cells.
Figure 8:
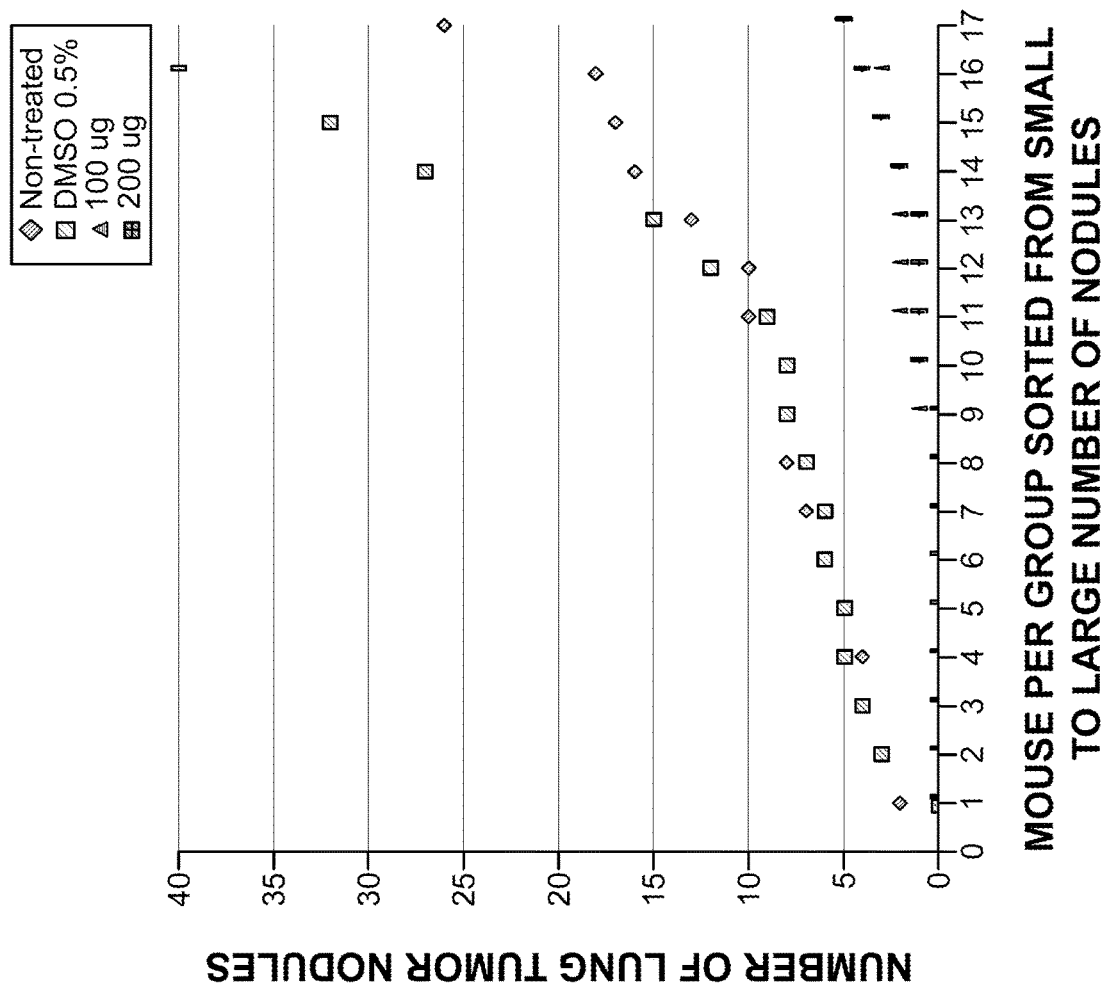
FIG. 8 shows a graphical illustration of the number of nodules per each mouse in a non-treated group (diamonds), a treated with DMSO group (light shaded squares), treated with 100 μg of IR5-01 group (triangles), or treated with 200 μg of IR5-01 group (dark shaded squares).
Figure 9:
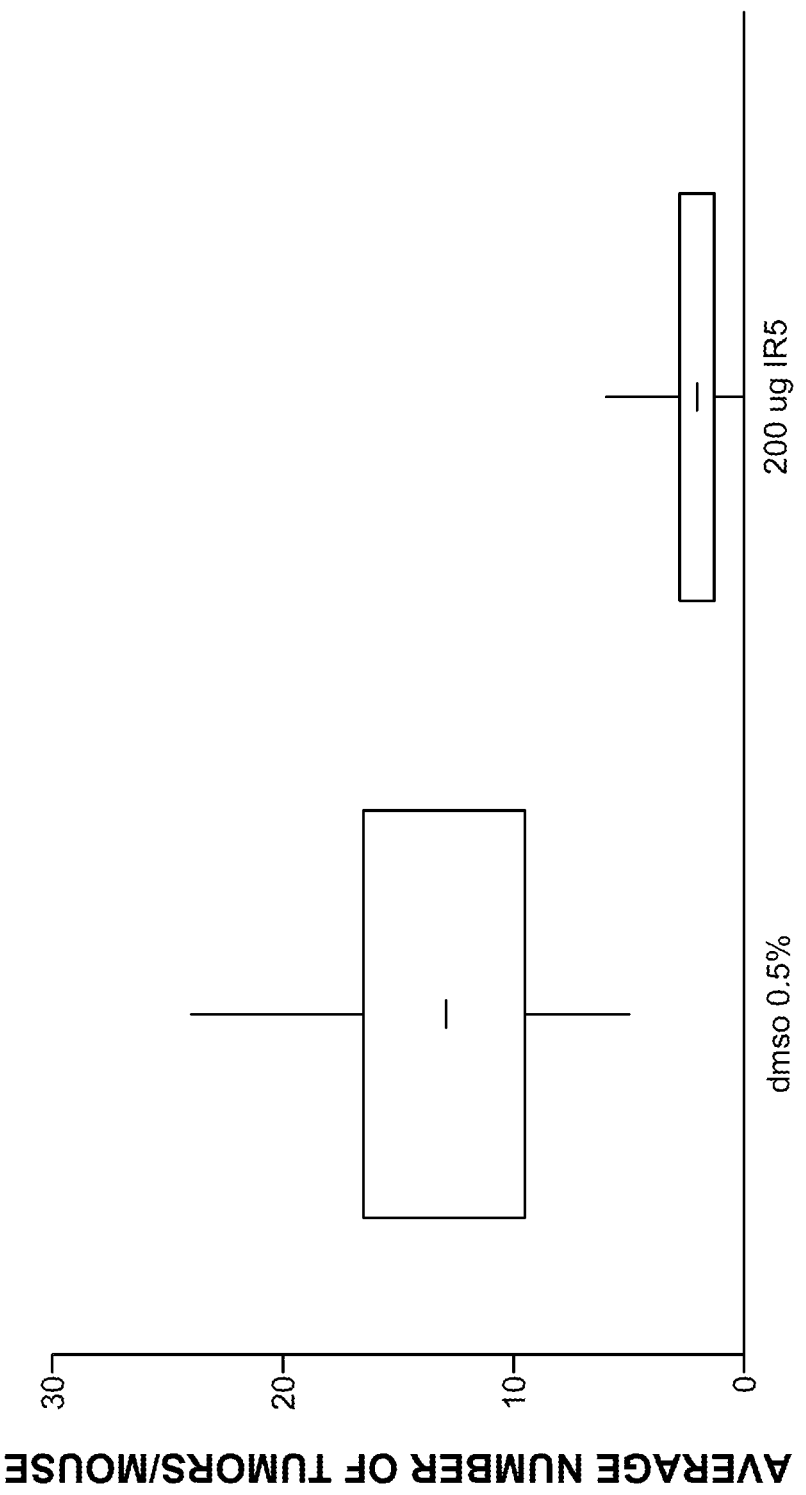
FIG. 9 shows a graphical illustration of the results of another representative experiment showing the average number of metastatic lung nodules (y-axis) on the lungs of C57BL/6 mice treated DMSO or 200 μg of IR5-01.

The cancer peptide agents described herein were identified using a novel bioinformatics method. In short, the bioinformatics method comprises compiling a list of proteins associated with cancer metastasis, which protein are termed cancer metastasis associated proteins (CMAPs). CMAPs are identified, in part, as proteins that are overexpressed in cancer metastasis. Non-liming examples of CMAPs are provided in Table 1. A network array is then generated where CMAPs are connected by shared sequence motifs which are identified as Cancer Metastasis Binding Peptides (CMBPs) (e.g., see Example 1 and FIG. 1A-FIG. 1C). CMBPs are further analyzed and scored (e.g., according to predicted protein-protein binding specificity and relative binding strengths) to identify the cancer peptide agents described herein. Non-limiting examples of certain cancer peptide agents are shown in FIG. 2.A1, FIG. 2.A2, FIG. 2B and FIG. 3.

A cancer peptide agent, in some embodiments, is between 8 and 50 amino acids long, between 8 and 30 amino acids long, between 8 and 20 amino acids long, between 8 and 15 amino acids long, or between about 8 and 12 amino acids long. In some embodiments, a cancer peptide agent is 8, 9, 10, 11, 12, 13, 14, or 15 amino acids long. In some embodiments, cancer peptide agents can be provided in mixtures or compositions comprising two or more cancer peptide agents. In some embodiments, where two or more cancer peptide agents are present, the cancer peptide agents can be arranged in a polypeptide in tandem where the two or more cancer peptides are linked by a covalent bond (e.g., a peptide bond or other suitable linkage).

In certain embodiments, a cancer peptide agent comprises or consists of the amino add sequence of DVWSXGXXXY (SEQ ID NO:1), DXWSXGCXXY (SEQ ID NO:2), DXWSXGXXLY (SEQ ID NO:3) or KSDXWSLGCXLY (SEQ ID NO:4), where X can be any amino acid. In certain embodiments, a cancer peptide agent comprises or consists of the amino acid sequence of $DX_1WSX_2GX_3X_4X_5Y$ (SEQ ID NO:16), where $X_1$ and $X_4$ is selected from I, V, and L, $X_2$ and $X_5$ is selected from I, V, L and M, and $X_3$ is selected from C, I, V, or L. In certain embodiments, a cancer peptide agent comprises or consists of the amino acid sequence of D(I/V)WS(L/M/I)G(C/I)(L/I)(L/M)Y (SEQ ID NO:5). In some embodiments, a cancer peptide agent comprises or consists of the amino acid sequence of DVWSLGCLLY (SEQ ID NO:6, IR13-01). The cancer peptide agent of SEQ ID NO:6 was derived from, in part, the amino acid sequence of dual specificity protein kinase TTK, isoform 1 (UniProtKB accession No. P33981). In some embodiments, a cancer peptide agent comprises or consists of the amino acid sequence of DVWSIGCIMY (SEQ ID NO:7, IR13-02). The cancer peptide agent of SEQ ID NO:7 was derived from, in part, the amino acid sequence of serine/threonine-protein kinase PLK1, isoform 1 (UniProtKB accession No. P53350). In some embodiments, a cancer peptide agent comprises or consists of the amino acid sequence of DVWSMGILLY (SEQ ID NO:8, IR5-02). The cancer peptide agent of SEQ ID NO:8 was derived from, in part, the amino acid sequence of maternal embryonic leucine zipper kinase (MELK), isoform 1 (UniProtKB accession No. Q14680). In some embodiments, a cancer peptide agent comprises or consists of the amino acid sequence of DIWSLGCLLY (SEQ ID NO:9, IR5-01). The cancer peptide agent of SEQ ID NO:9 was derived from, in part, the amino acid sequence of serine/threonine-protein kinase Nek2 (NEK2; Nek2A), isoform 1 (UniProtKB accession No. P51955). In some embodiments, a cancer peptide agent comprises or consists of the amino acid sequence of DVWSLGCLLY (SEQ ID NO:14). In some embodiments, a cancer peptide agent comprises or consists of the amino acid sequence of KSDVWSLGCILY (SEQ ID NO:10), KSKISPKSDVWSLGCILYYMT (SEQ ID NO:11), DVWSIGCIMYTLLVGKPPFET (SEQ ID NO:12), GKYDVPKWLSPSSILLLQQML (SEQ ID NO:13), or NEKSDIWSLGCLLYELCALMP (SEQ ID NO:15).

In some embodiments a cancer peptide agent comprises a label. As used herein, the terms "label" or "labeled" refers to incorporation of a detectable marker, e.g., by incorporation of a labeled amino acid or attachment to a polypeptide of biotin moieties that can be detected by labeled avidin (e.g., streptavidin containing a fluorescent marker or enzymatic activity that can be detected by optical or colorimetric methods). In certain embodiments, a label or marker can be attached to a cancer peptide agent to generate a therapeutic or diagnostic agent. A cancer peptide agent can be attached covalently or non-covalently to any suitable label or marker. Various methods of labeling polypeptides and glycoproteins are known to those skilled in the art and can be used. Non-limiting examples of labels for polypeptides include, but are not limited to, the following: radioisotopes or radionuclides (e.g., $^{3}$H, $^{14}$C, $^{15}$N, $^{35}$S, $^{90}$Y, $^{99}$Tc, $^{125}$I, $^{131}$I), fluorescent labels, enzymatic labels (e.g., horseradish peroxidase, β-galactosidase, luciferase, alkaline phosphatase), chemiluminescent labels, a metallic label, a chromophore, an electro-chemiluminescent label, a phosphorescent label, a quencher (e.g., a fluorophore quencher), a fluorescence resonance energy transfer (FRET) pair (e.g., donor and acceptor), a dye, an enzyme substrate, a small molecule, a mass tag, quantum dots, nanoparticles, biotinyl groups, predetermined polypeptide epitopes recognized by a secondary reporter (e.g., leucine zipper pair sequences, binding sites for secondary antibodies, metal binding domains, epitope tags), the like or combinations thereof.

In some embodiments a cancer peptide agent comprises a suitable therapeutic agent. A cancer peptide agent can be attached covalently or non-covalently to any suitable therapeutic agent. Non-limiting examples of a therapeutic agent include a medication, toxin, radioisotope, ligand, receptor, cytokine, antibody, anti-neoplastic agent, inhibitor (e.g., a receptor antagonist, an enzyme inhibitor), a cytokine or an agent disclosed in U.S. Pat. No. 6,660,843, which is incorporated herein by reference, the like or combinations thereof. Non-limiting examples of anti-neoplastic agents include an auristatin (e.g., monomethyl auristatin E (MMAE), monomethyl auristatin F (MMAF), and the like), a dolastatin, a maytansine, a tubulysin, an irinotecan or derivative or metabolite thereof (e.g., SN38), a calicheamicin, a pyrrolobenzodiazepine (PBD), a duocarmycin, a doxorubicin, a pseudomonas exotoxin A (e.g., PE38), derivatives thereof, the like or combinations thereof. Accordingly, in certain embodiments, a cancer peptide agent disclosed herein comprises an anti-neoplastic agent.

In some embodiments a cancer peptide agent comprises a suitable carrier. A cancer peptide agent can be attached covalently or non-covalently to a suitable carrier. Suitable carriers include agents or molecules that alter or extend the in vivo half-life of a cancer peptide agent, non-limiting examples of which include polyethylene glycol, glycogen (e.g., by glycosylation of a cancer peptide agent), a dextran, a carrier or vehicle described in U.S. Pat. No. 6,660,843, the like or combinations thereof.

In some embodiments a label, therapeutic agent or carrier is bound to a cancer peptide agent by use of a suitable linker. Non-limiting examples of a suitable linker include silanes, thiols, phosphonic acid, polyethylene glycol (PEG), amino acids and peptides, polymers thereof, derivatives thereof, the like and combinations thereof. Methods of attaching two or more molecules using a linker are known to those skilled in the art and are sometimes referred to as "crosslinking."

In some embodiments a label, therapeutic agent, carrier or linker is attached to a suitable thiol group of a cancer peptide agent (e.g., a thiol group of a cysteine residue). In some embodiments, a thiol group is added to a cancer peptide agent (e.g., by addition of a cysteine residue). Other non-limiting examples of attaching a label, therapeutic agent, carrier and/or linker to a cancer peptide agent include reacting an amine with an N-hydroxysuccinimide (NHS) ester, an imidoester, a pentafluorophenyl (PFP) ester, a hydroxymethyl phosphine, an oxirane or any other carbonyl compound; reacting a carboxyl with a carbodiimide; reacting a sulfhydryl with a maleimide, a haloacetyl, a pyridyldisulfide, and/or a vinyl sulfone; reacting an aldehyde with a hydrazine; reacting any non-selective group with diazirine and/or aryl azide; reacting a hydroxyl with isocyanate; reacting a hydroxylamine with a carbonyl compound; the like and combinations thereof.

In certain embodiments a cancer peptide agent is modified to include certain amino acid additions, substitutions, or deletions designed or intended, for example, to reduce susceptibility of a cancer peptide agent to proteolysis, reduce susceptibility of a cancer peptide agent to oxidation, increase serum half-life and/or confer or modify other physicochemical, pharmacokinetic or functional properties of a cancer peptide agent. In certain embodiments a cancer peptide agent is modified to include certain amino acid additions, substitutions, or deletions designed or intended to increase efficacy (e.g., the anti-metastatic properties) of a cancer peptide agent. Accordingly, a cancer peptide agent may comprise or consists of an amino acid sequence that is at least 70%, at least 75%, at least 80%, at least 85%, at least 90% or at least 95% identical (e.g., percent sequence identity) to a cancer peptide agent of any one of SEQ ID NOs: 1 to 16. In some embodiments, a cancer peptide agent shares at least 90% sequence identity to the amino acid sequence of a cancer peptide agent described herein (e.g., any of SEQ ID Nos: 1 to 16).

The term "percent identical" or "percent identity" refers to sequence identity between two amino acid sequences. Identity can be determined by comparing a position in each sequence which may be aligned for purposes of comparison. When an equivalent position in the compared sequences is occupied by the same amino acid, then the molecules are identical at that position. When the equivalent site is occupied by the same or a similar amino acid residue (e.g., similar in steric and/or electronic nature), then the molecules can be referred to as homologous (similar) at that position. Expression as a percentage of homology, similarity, or identity refers to a function of the number of identical or similar amino acids at positions shared by the compared sequences. Expression as a percentage of homology, similarity, or identity refers to a function of the number of identical or similar amino acids at positions shared by the compared sequences. Various alignment algorithms and/or programs may be used to determine percent identity, including FASTA, BLAST, or ENTREZ. FASTA and BLAST are available as a part of the GCG sequence analysis package (University of Wisconsin, Madison, Wis.), and can be used with, e.g., default settings. ENTREZ is available through the National Center for Biotechnology Information, National Library of Medicine, National Institutes of Health, Bethesda, Md. In one embodiment, the percent identity of two sequences can be determined by the GCG program with a gap weight of 1, e.g., each amino acid gap is weighted as if it were a single amino acid or nucleotide mismatch between the two sequences.

In some embodiments, a cancer peptide agent comprises one or more suitable modifications or modified amino acids non-limiting examples of which include D-amino acids, amino acids modified by acetylation, acylation, phosphorylation, glycosylation, myristoylation, amidation, hydroxylation (e.g., aspartic acid/asparagine hydroxylation), phosphopantethane attachment, methylation, methylthiolation, prenylation, addition of an intein, ADP-ribosylation, bromination, citrullination, deamination, dihdroxylation, formylation, geranyl-geranylation, glycation or palmitoylation.

TABLE 1

| | Name | ID | Description |
|---|---|---|---|
| 1 | TOP2A | P11388 | sp | P11388 | TOP2A_HUMAN DNA topoisomerase 2-alpha OS = *Homo sapiens* GN = TOP2A PE = 1 SV = 3 < /Description |
| 2 | CCNA2 | P20248 | sp | P20248 | CCNA2_HUMAN Cyclin-A2 OS = *Homo sapiens* GN = CCNA2 PE = 1 SV = 2 |
| 3 | CDK1 | P06493 | sp | P06493 | CDK1_HUMAN Cyclin-dependent kinase 1 OS = *Homo sapiens* GN = CDK1 PE = 1 SV = 3 |
| 4 | MD2L1 | Q13257 | sp | Q13257 | MD2L1_HUMAN Mitotic spindle assembly checkpoint protein MAD2A OS = *Homo sapiens* GN = MAD2L1 PE = 1 SV = 1 |
| 5 | AURKA | O14965 | sp | O14965 | AURKA_HUMAN Aurora kinase A OS = *Homo sapiens* GN = AURKA PE = 1 SV = 2 |
| 6 | CDC20 | Q12834 | sp | Q12834 | CDC20_HUMAN Cell division cycle protein 20 homolog OS = *Homo sapiens* GN = CDC20 PE = 1 SV = 2 |
| 7 | CENPF | P49454 | sp | P49454 | CENPF_HUMAN Centromere protein F OS = *Homo sapiens* GN = CENPF PE = 1 SV = 2 |
| 8 | PTTG1 | O95997 | sp | O95997 | PTTG1_HUMAN Securin OS = *Homo sapiens* GN = PTTG1 PE = 1 SV = 1 |
| 9 | UBE2C | O00762 | sp | O00762 | UBE2C_HUMAN Ubiquitin-conjugating enzyme E2 C OS = *Homo sapiens* GN = UBE2C PE = 1 SV = 1 |
| 10 | FOXM1 | Q08050 | sp | Q08050 | FOXM1_HUMAN Forkhead box protein M1 OS = *Homo sapiens* GN = FOXM1 PE = 1 SV = 3 |
| 11 | CCNB1 | P14635 | sp | P14635 | CCNB1_HUMAN G2/mitotic-specific cyclin-B1 OS = *Homo sapiens* GN = CCNB1 PE = 1 SV = 1 |
| 12 | CCNB2 | O95067 | sp | O95067 | CCNB2_HUMAN G2/mitotic-specific cyclin-B2 OS = *Homo sapiens* GN = CCNB2 PE = 1 SV= |
| 13 | CDC6 | Q99741 | sp | Q99741 | CDC6_HUMAN Cell division control protein 6 homolog OS = *Homo sapiens* GN = CDC6 PE = 1 SV = 1 |
| 14 | CENPA | P49450 | Sp | P49450 | CENPA_HUMAN Histone H3-like centromeric protein A OS = *Homo sapiens* GN = CENPA PE = 1 SV = 1 |
| 15 | EZH2 | Q15910 | sp | Q15910 | EZH2_HUMAN Histone-lysine N-methyltransferase EZH2 OS = *Homo sapiens* GN = EZH2 PE = 1 SV = 2 |
| 16 | NEK2 | P51955 | sp | P51955 | NEK2_HUMAN Serine/threonine-protein kinase Nek2 OS = *Homo sapiens* GN = NEK2 PE = 1 SV = 1 |
| 17 | TTK | P33981 | sp | P33981 | TTK_HUMAN Dual specificity protein kinase TTK OS = *Homo sapiens* GN = TTK PE = 1 SV = 2 |
| 18 | TTK-12 | P33981 | sp | P33981 | ITTK_HUMAN Dual specificity protein kinase TTK OS = *Homo sapiens* GN = TTK PE = 1 SV = 2 |
| 19 | UBE2S | Q16763 | sp | Q16763 | UBE2S_HUMAN Ubiquitin-conjugating enzyme E2 S OS = *Homo sapiens* GN = UBE2S PE = 1 SV= |
| 20 | RFC4 | P35249 | sp | P35249 | RFC4_HUMAN Replication factor C subunit 4 OS = *Homo sapiens* GN = RFC4 PE = 1 SV = 2 |
| 21 | GGH | Q92820 | sp | Q92820 | GGH_HUMAN Gamma-glutamyl hydrolase OS = *Homo sapiens* GN = GGH PE = 1 SV = 2 |
| 22 | KIF23 | Q02241 | sp | Q02241 | KIF23_HUMAN Kinesin-like protein KIF23 OS = *Homo sapiens* GN = KIF23 PE = 1 SV = 3 |
| 23 | PLK1 | P53350 | sp | P53350 | PLK1_HUMAN Serine/threonine-protein kinase PLK1 OS = *Homo sapiens* GN = PLK1 PE = 1 SV = 1 |
| 24 | BIRC5 | O15392 | sp | O15392 | BIRC5_HUMAN Baculoviral IAP repeat-containing protein 5 OS = *Homo sapiens* GN = BIRC5 PE = 1 SV = 3 |
| 25 | BUB1 | O43683 | sp | O43683 | BUB1_HUMAN Mitotic checkpoint serine/threonine-protein kinase BUB1 OS = *Homo sapiens* GN = BUB1 PE = 1 SV = 1 |
| 26 | MPIP3 | P30307 | sp | P30307 | MPIP3_HUMAN M-phase inducer phosphatase 3 OS = *Homo sapiens* GN = CDC25C PE = 1 SV = 2 |
| 27 | BOREA | Q53350 | sp | Q53HL2 | BOREA_HUMAN Borealin OS = *Homo sapiens* GN = CDCA8 PE = 1 SV = 2 |

TABLE 1-continued

| | Name | ID | Description |
|---|---|---|---|
| 28 | CENPE | Q02224 | sp | Q02224 | CENPE_HUMAN Centromere-associated protein E OS = *Homo sapiens* GN = CENPE PE = 1 SV = 2 |
| 29 | CKS2 | P33552 | sp | P33552 | CKS2_HUMAN Cyclin-dependent kinases regulatory subunit 2 OS = *Homo sapiens* GN = CKS2 PE = 1 SV = 1 |
| 30 | DLGP5 | Q15393 | sp | Q15398 | DLGP5_HUMAN Disks large-associated protein 5 OS = *Homo sapiens* GN = DLGAP5 PE = 1 SV = 2 |
| 31 | ESPL1 | Q14674 | sp | Q14674 | ESPL1_HUMAN Separin OS = *Homo sapiens* GN = ESPL1 PE = 1 SV = 3 |
| 32 | FEN1 | P39748 | sp | P39748 | FEN1_HUMAN Flap endonuclease 1 OS = *Homo sapiens* GN = FEN1 PE = 1 SV = 1 |
| 33 | H2AX | P16104 | sp | P16104 | H2AX_HUMAN Histone H2AX OS = *Homo sapiens* GN = H2AFX PE = 1 SV = 2 |
| 34 | KIF14 | Q15058 | sp | Q15058 | KIF14_HUMAN Kinesin-like protein KIF14 OS = *Homo sapiens* GN = KIF14 PE = 1 SV = 1 |
| 35 | KIF2C | Q99661 | sp | Q99661 | KIF2C_HUMAN Kinesin-like protein KIF2C OS = *Homo sapiens* GN = KIF2C PE = 1 SV = 2 |
| 36 | KIFC1 | Q9BW19 | sp | Q9BW19 | KIFC1_HUMAN Kinesin-like protein KIFC1 OS = *Homo sapiens* GN = KIFC1 PE = 1 SV = 2 |
| 37 | PCH2 | Q15645 | sp | Q15645 | PCH2_HUMAN Pachytene checkpoint protein 2 homolog OS = *Homo sapiens* GN = TRIP13 PE = 1 SV = 2 |
| 38 | MELK | Q14680 | sp | Q14680 | MELK_HUMAN Maternal embryonic leucine zipper kinase OS = *Homo sapiens* GN = MELK PE = 1 SV = 3 |
| 39 | PCNA | P12004 | sp | P12004 | PCNA_HUMAN Proliferating cell nuclear antigen OS = *Homo sapiens* GN = PCNA PE = 1 SV = 1 |
| 40 | PRC1 | O43663 | sp | O43663 | PRC1_HUMAN Protein regulator of cytokinesis 1 OS = *Homo sapiens* GN = PRC1 PE = 1 SV = 2 |
| 41 | RIR2 | P31350 | sp | P31350 | RIR2_HUMAN Ribonucleoside-diphosphate reductase subunit M2 OS = *Homo sapiens* GN = RRM2 PE = 1 SV = 1 |
| 42 | RIR2 | P31350 | Sp | P31350 | RIR2_HUMAN Ribonucleoside-diphosphate reductase subunit M2 OS = *Homo sapiens* GN = RRM2 PE = 1 SV = 1 |
| 43 | TPX2 | Q9ULWO | sp | Q9ULWO | TPX2_HUMAN Targeting protein for Xklp2 OS = *Homo sapiens* GN = TPX2 PE = 1 SV2 |
| 44 | MYBB | P10244 | sp | P10244 | MYBB_HUMAN Myb-related protein B OS *Homo sapiens* GN = MYBL2 PE = 1 SV = 1 |
| 45 | ATAD2 | Q6PL1B | sp | Q6PL18 | ATAD2_HUMAN ATPase family AAA domain-containing protein 2 OS = *Homo sapiens* GN = ATAD2 PE = 1 SV = 1 |
| 46 | CEP55 | Q53EZ4 | sp | Q53EZ4 | CEP55_HUMAN Centrosomal protein of 55 kDa OS = *Homo sapiens* GN = CEP55 PE = 1 SV = 3 |
| 47 | ZWINT | O95229 | sp | O95229 | ZWINT_HUMAN ZW10 interactor OS = *Homo sapiens* GN = ZWINT PE = 1 SV= |
| 48 | CDK1 | P06493 | sp | P06493 | CDK1_HUMAN Cyclin-dependent kinase 1 OS = *Homo sapiens* GN = CDK1 PE1 SV= |
| 49 | AURKA | O14965 | sp | O14965 | AURKA_HUMAN Aurora kinase A OS = *Homo sapiens* GN = AURKA PE = 1 SV = 2 |
| 50 | CENPF | P49454 | sp | P49454 | CENPF_HUMAN Centromere protein F OS = *Homo sapiens* GN = CENPF PE = 1 SV = 2 |
| 51 | EZH2 | Q15910 | sp | Q15910 | EZH2_HUMAN Histone-lysine N-methyltransferase EZH2 OS = *Homo sapiens* GN = EZH2 PE = 1 SV = 2 |
| 52 | NEK2 | P51955 | sp | P51955 | NEK2_HUMAN Serine/threonine-protein kinase Nek2 OS = *Homo sapiens* GN = NEK2 PE = 1 SV = 1 |
| 53 | TTK | P33981 | sp | P33981 | TTK_HUMAN Dual specificity protein kinase TTK OS = *Homo sapiens* GN = TTK PE = 1 SV = 2 |
| 54 | K1F23 | Q02241 | sp | Q02241 | K1F23_HUMAN Kinesin-like protein KIF23 OS = *Homo sapiens* GN = KIF23 PE = 1 SV = 3 |
| 55 | CENPE | Q02224 | sp | Q02224 | CENPE_HUMAN Centromere-associated protein E OS = *Homo sapiens* GN = CENPE PE = 1 SV = 2 |
| 56 | KIF14 | Q15058 | sp | Q15058 | K1F14_HUMAN Kinesin-like protein KIF14 OS = *Homo sapiens* GN = KIF14 PE = 1 SV = 1 |
| 57 | KIF2C | Q99661 | sp | Q99661 | KIF2C_HUMAN Kinesin-like protein KIF2C OS = *Homo sapiens* GN = KIF2C PE = 1 SV= |
| 58 | KIFC1 | Q9BW19 | sp | Q9BW19 | KlFC1_HUMAN Kinesin-like protein KIFC1 OS = *Homo sapiens* GN = KIFC1 PE = 1 SV = 2 |
| 59 | MELK | Q14680 | sp | Q14680 | MELK_HUMAN Maternal embryonic leucine zipper kinase OS = *Homo sapiens* GN = MELK PE = 1 SV = 3 |
| 60 | NFKB2 | Q00653 | sp | Q00653 | NFKB2_HUMAN Nuclear factor NF-kappa-B p100 subunit OS = *Homo sapiens* GN = NFKB2 PE = 1 SV = 4 |
| 61 | NFKB1 | P19838 | sp | P19838 | NFKB1_HUMAN Nuclear factor NF-kappa-B p105 subunit OS = *Homo sapiens* GN = NFKB1 PE = 1 SV = 2 |
| 62 | TF65 | Q04206 | sp | Q04206 | TF65_HUMAN Transcription factor p65 OS = *Homo sapiens* GN = RELA PE = 1 SV = 2 |
| 63 | RELB | Q01201 | sp | Q01201 | RELB_HUMAN Transcription factor RelB OS = *Homo sapiens* GN = RELB PE = 1 SV = 2 |
| 64 | REL | Q04864 | sp | Q04864 | REL_HUMAN Proto-oncogene c-Rel OS = *Homo sapiens* GN = REL PE = 1 SV = 1 |
| 65 | P53 | P04637 | sp | P04637 | P53_HUMAN Cellular tumor antigen p53 OS = *Homo sapiens* GN = TP53 PE = 1 SV = 4 |

Chemotherapeutic Agents & Combination Treatments

In some embodiments, a method comprises administering a therapeutically effective amount of one or more cancer peptide agents and a therapeutically effective amount of a chemotherapy to a subject having or suspected of having a cancer. In some embodiments, a method comprises administering a therapeutically effective amount of a pharmaceutical composition described herein and a therapeutically effective amount of a chemotherapy to a subject having or suspected of having a cancer. In some embodiments, administering a chemotherapy comprises administering a therapeutically effective amount of a chemotherapeutic agent. In some embodiments, administering a chemotherapy comprises administering a therapeutically effective amount of a radiation therapy or radiation treatment.

In some embodiments a chemotherapeutic agent comprises or consists of one or more cytotoxic compounds. Cytotoxic compounds can be organic or inorganic compounds. In some embodiments cytotoxic compounds are relatively small compounds with a molecular weight between 1 and about 20,000 Daltons, 1 and about 10,000 Daltons, 1 and about 5000 Daltons, 1 and about 2500 Daltons, 1 and about 1000 Daltons, 1 and about 500 Daltons or between about 50 and about 1000 Daltons.

Any suitable chemotherapeutic agent can be used for a method described herein. In some embodiments a chemotherapeutic agents is a protein or polypeptide. In some embodiments a chemotherapeutic agents is an antibody (e.g., a monoclonal or polyclonal antibody). Chemotherapeutic agents can be polypeptides or fusion proteins. In some embodiments, chemotherapeutic agents are not cytotoxic until after they are administered to a subject wherein the chemotherapeutic agents are metabolized into a cytotoxic compound (e.g., cyclophosphamide). In some embodiments a cell is contacted with a chemotherapeutic agent and the cell metabolizes the chemotherapeutic agent into a cytotoxic compound. A cell can be contacted directly or indirectly (e.g., by a targeted approach) with a chemotherapeutic agent.

In some embodiments a chemotherapeutic agent comprises or consists of an alkylating agent, an anthracycline, cytoskeletal disruptors, epothilones (e.g., epothilone), histone deacetylase inhibitors (e.g., vorinostat, romidepsin), inhibitors of topoisomerase I (e.g., irinotecan, topotecan), inhibitors of topoisomerase II (e.g., etoposide, teniposide, tafluposidean), kinase inhibitors, peptide antibiotics (e.g., bleomycin, actinomycin), platinum-based agents (e.g., carboplatin, cisplatin, oxaliplatin), retinoids (e.g., tretinoin, alitretinoin, bexarotene), vinca alkaloids and derivatives (e.g., vinblastine, vincristine, vindesine, vinorelbine), antimetabolites, plant extracts, plant alkaloids, nitrosourea, hormone, nucleoside or nucleotide analog and combinations thereof.

In some embodiments a chemotherapeutic agent comprises an alkylating anti-neoplastic agent (e.g., an alkylating anti-neoplastic agent). An alkylating antineoplastic agent is a class of chemotherapeutic agents that work, in part, by attaching an alkyl group (e.g., CnH2n+1) to DNA, a process known alkylation. Some alkylating antineoplastic agents are administered as a pro-drug that is converted in vivo to an active alkylating agent. An alkylating antineoplastic agent often alkylates a guanine base of DNA. Alkylating antineoplastic agents are most effective on proliferating cells (e.g., cancer cells) which, in general, proliferate faster and with less error-correcting than healthy cells. Non-limiting examples of alkylating anti-neoplastic agents include Altretamine (hexamethylmelamine, HEXALEN®), Busulfan, Carmustine (BCNU), Chlorambucil, Cyclophosphamide, Dacarbazine (DTIC), Fotemustine, Ifosfamide, Lomustine (CCNU), Mechlorethamine, Melphalan, Procarbazine, semustine (MeCCNU), Streptozotocin, Temozolomide, Thiotepa (triethylenethio-phosphoramide), Carboplatin, Cisplatin, Oxaliplatin, monofunctional alkylators, nitrosoureas, temozolomide, the like or combinations thereof.

In some embodiments a chemotherapeutic agent comprises a DNA intercalating agent which is often an agent that attaches or bonds to DNA or RNA. Non-limiting examples of a DNA intercalating agent include acrolein, anthracycline, phosphoramide, Actinomycin D, bleomycin, idarubicin, daunorubicin, doxorubicin, elsamicin A, epirubicin, ethidium, m-AMSA, mitoxantrone, doxorubicin (Adriamycin, Doxil, Myocet, hydroxydaunorubicin, hydroxydaunomycin), Epirubicin, Idarubicin, Valrubicin, TAS-103, MLN944 (XR5944), Obatoclax, mechlorethamine, methotrexate, 6-mercaptopurine, thioguanine, 5-fluorouracil, cytosine arabinoside, 5-azacytidine (5-AZC) and 5-azacytidine related compounds, mithramycin, mitomycin C, hydroxyurea, carboplatin, oxiplatin, mitotane, a taxane, vinblastine, vincristine, dibromomannitol, gemcitabine, pemetrexed, the like or a combination thereof.

In some embodiments a chemotherapeutic agent comprises a cytoskeletal disruptor. Non-limiting examples of cytoskeletal disruptors (e.g., taxanes) include paclitaxel, taxol, and docetaxel.

In some embodiments a chemotherapeutic agent comprises a kinase inhibitor. Non-limiting examples of kinase inhibitors include bortezomib, erlotinib, gefitinib, imatinib, vemurafenib, vismodegib, the like, analogs and derivatives thereof.

In some embodiments a chemotherapeutic agent comprises one or more nucleotide analogs. Non-limiting examples of nucleotide analogs include azacitidine, azathioprine, capecitabine, cytarabine, doxifluridine, fluorouracil, gemcitabine, hydroxyurea, mercaptopurine, methotrexate, tioguanine (formerly thioguanine), the like, analogs and derivatives thereof.

Cancers & Metastasis

In some embodiments a method or composition disclosed herein is for use in treating a subject having or suspected of having a cancer. A cancer may be benign, malignant, metastatic, or non-metastatic. In certain embodiments, a cancer is a malignant or metastatic cancer. Non-limiting examples of a cancer include melanoma, lymphoma (e.g., Hodgkin lymphoma, non-Hodgkin lymphoma, a B-cell neoplasm, a T-cell neoplasm, an NK cell neoplasm), leukemia, reticuloendothelial hyperplasia (e.g., reticuloendothelial neoplasia), lymphatic neoplasia, hematopoietic neoplasia, myeloma, multiple myeloma, an immunodeficiency-associated lymphoproliferative disorder, adenoma, adenocarcinoma, sarcoma (non-limiting examples of which include a lymphosarcoma, liposarcoma, osteosarcoma, chondrosarcoma, leiomyosarcoma, rhabdomyosarcoma, fibrosarcoma, the like or combinations thereof), carcinoma, breast cancer, colorectal cancer, gastrointestinal cancer, hepatocellular cancer, lung cancer, bone cancer, renal cancer, bladder cancer, hepatoma, neuroblastoma, retinoblastoma, astrocytoma, glioma, glioblastoma, medulloblastoma, meningioma, oligodendrocytoma, cervical cancer, testicular cancer, ovarian cancer, mesothelioma, esophageal cancer, pancreatic cancer, prostate cancer, the like or combinations thereof.

In some embodiments a cancer comprises a metastatic melanoma. In some embodiments a cancer comprises a lung, thyroid, head or neck, nasopharynx, throat, nose or sinuses, brain, spine, breast, adrenal gland, pituitary gland, thyroid, lymph, gastrointestinal (mouth, esophagus, stomach, duodenum, ileum, jejunum (small intestine), colon, rectum), genito-urinary tract (uterus, ovary, cervix, endometrial, bladder, testicle, penis, prostate), kidney, pancreas, liver, bone, bone marrow, lymph, blood, muscle, or skin, lung, biliary tract, or hematologic neoplasia, tumor, or cancer. In some embodiments a cancer comprises a solid cellular mass. In certain embodiments a malignant cancer comprises or consists of a fibrosarcoma, myxosarcoma, liposarcoma, chondrosarcoma, osteosarcoma, chordoma, malignant fibrous histiocytoma, hemangiosarcoma, angiosarcoma, lymphangiosarcoma, mesothelioma, leiomyosarcoma, rhabdomyosarcoma, squamous cell carcinoma, epidermoid carcinoma, malignant skin adnexal tumor, adenocarcinoma, hepatoma, hepatocellular carcinoma, renal cell carcinoma, hypernephroma, cholangiocarcinoma, transitional cell carcinoma, choriocarcinoma, seminoma, embryonal cell carcinoma, glioma, glioblastoma multiforme, neuroblastoma, medulloblastoma, malignant meningioma, malignant schwannoma, neurofibrosarcoma, parathyroid carcinoma, medullary carcinoma of thyroid, bronchial carcinoid, oat cell carcinoma, malignant pheochromocytoma, islet cell carcinoma, malignant carcinoid, retinoblastoma, chemodectoma, paraganglioma, malignant carcinoid, malignant paraganglioma, melanoma, malignant schwannoma, merkel cell neoplasm, cystosarcoma phylloides, wilms tumor, malignant ovarian tumors, malignant testicular tumors, the like, or combinations thereof. In certain embodiments a cancer comprises a carcinoma, sarcoma, lymphoma, leukemia, adenoma, adenocarcinoma, melanoma, glioma, glioblastoma, medulloblastoma, Kaposi sarcoma, meningioma, neuroblastoma, retinoblastoma, astrocytoma, oligodendrocytoma, reticuloendothelial, lymphatic or haematopoietic neoplasia, tumor, cancer or malignancy. In certain embodiments a sarcoma comprises a lymphosarcoma, liposarcoma, osteosarcoma, chondrosarcoma, leiomyosarcoma, rhabdomyosarcoma or fibrosarcoma.

In some embodiments a leukemia is an acute lymphocytic leukemia (ALL), acute myeloid leukemia (AML), chronic lymphocytic leukemia (CLL), chronic myeloid leukemia (CML), or chronic myelomonocytic leukemia (CMML).

Pharmaceutical Compositions, Administration and Dosing

In certain embodiments, a pharmaceutical composition comprises one or more cancer peptide agents. In certain embodiments, a pharmaceutical composition comprises at least 2, at least 3 or at least 4 cancer peptide agents. In certain embodiments, a pharmaceutical composition comprises 1 to 20, 1 to 10, or 1 to 5 cancer peptide agents. In certain embodiments, a pharmaceutical composition comprises 1, 2, 3, 4, 5, 6, 7, 8 or more cancer peptide agents.

In some embodiments, a pharmaceutical composition is delivered to a subject or cancer cell via one or more delivery systems depending on the indication, disease state, severity, clinical utility and other relevant parameters that may impact the desired efficacy of a treatment using one or more cancer peptide agents described herein.

The exact formulation and route of administration of a cancer peptide agent (e.g., one or more cancer peptide agents) or a composition for use according to the methods of the invention described herein can be chosen by the individual physician in view of a patient's condition. See e.g., Fingl et al. 1975, in "The Pharmacological Basis of Therapeutics," Ch. 1 p. 1; which is incorporated herein by reference in its entirety. Any suitable route of administration can be used for administration of a composition (e.g., a pharmaceutical composition) or a cancer peptide agent described herein. Non-limiting examples of routes of administration include topical or local (e.g., transdermally or cutaneously, (e.g., on the skin or epidermis), in or on the eye, intranasally, transmucosally, in the ear, inside the ear (e.g., behind the ear drum)), enteral (e.g., delivered through the gastrointestinal tract, e.g., orally (e.g., as a tablet, capsule, granule, liquid, emulsification, lozenge, or combination thereof), sublingual, by gastric feeding tube, rectally, and the like), by parenteral administration (e.g., parenterally, e.g., intravenously, intra-arterially, intramuscularly, intraperitoneally, intradermally, subcutaneously, intracavity, intracranially, intraarticular, into a joint space, intracardiac (into the heart), intracavernous injection, intralesional (into a skin lesion), intraosseous infusion (into the bone marrow), intrathecal (into the spinal canal), intrauterine, intravaginal, intratumoral, intravesical infusion, intravitreal), the like or combinations thereof.

In some embodiments one or more cancer peptide agents or a composition described herein is provided to a subject. A composition that is provided to a subject is sometimes provided to a subject for self-administration or for administration to a subject by another (e.g., a non-medical professional). For example a composition described herein can be provided with an instruction written by a medical practitioner that authorizes a patient to be provided a composition or treatment described herein (e.g., a prescription). In another example, a composition can be provided to a subject wherein the subject self-administers a composition orally, intravenously, topically or by way of an inhaler, for example.

One or more cancer peptide agents and compositions (e.g., compositions comprising a one or more cancer peptide agents) can be formulated to be compatible with a particular route of administration or use. Compositions for parenteral, intradermal, or subcutaneous administration can include a sterile diluent, such as water, saline solution, fixed oils, polyethylene glycols, glycerin, propylene glycol or other synthetic solvents. A pharmaceutical composition may contain one or more preservatives to prevent microorganism growth (e.g., antibacterial agents such as benzyl alcohol or methyl parabens; antioxidants such as ascorbic acid or sodium bisulfite; chelating agents such as EDTA; buffers such as acetates, citrates or phosphates and agents for the adjustment of tonicity such as sodium chloride or dextrose). Antibacterial and antifungal agents include, for example, parabens, chlorobutanol, phenol, ascorbic acid and thimerosal.

Compositions for injection include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, NJ) or phosphate buffered saline (PBS). The carrier can be a solvent or dispersion medium containing, for example, water, ethanol, polyol (e.g., glycerol, propylene glycol, and polyethylene glycol), and suitable mixtures thereof. Fluidity can be maintained, for example, by the use of a coating such as lecithin, or by the use of surfactants. In some embodiments, a pharmaceutical composition includes an agent that delays absorption, for example, aluminum monostearate and gelatin which can prolong absorption of injectable compositions. In some embodiments, a pharmaceutical composition comprises polysorbate 20 or polysorbate 80, for example, up to 1%. Other non-limiting additives include histidine HCl, and α,α-trehalose dehydrate.

In some embodiments, one can administer compositions for use according to the methods of the invention in a local rather than systemic manner, for example, via direct application to the skin, mucous membrane or region of interest for treating, including using a depot or sustained release formulation.

In some embodiments, active ingredients (e.g., one or more cancer peptide agents) can be administered alone or formulated as a composition (e.g., a pharmaceutical composition). In other embodiments, a one or more cancer peptide agents can be administered in combination with one or more additional materials (e.g., one or more chemotherapeutic agents or cytokines), for example, as two separate compositions or as a single composition where the additional material(s) is (are) mixed or formulated together with a one or more cancer peptide agents. For example, without being limited thereto, a one or more cancer peptide agents can be formulated with additional excipients, or additional active ingredients.

The pharmaceutical compositions can be manufactured by any suitable manner, including, e.g., by means of conventional mixing, dissolving, granulating, dragee-making, levigating, emulsifying, encapsulating, entrapping or tableting processes.

Pharmaceutical compositions comprising one or more cancer peptide agents described herein for use in accordance with the invention can be formulated in any suitable manner using one or more pharmaceutically acceptable carriers, solvents, salts, excipients, additives, preservatives, and/or auxiliaries. Proper formulation can depend upon the route of administration chosen. In particular, a pharmaceutical compositions can comprise any suitable formulation, ingredient, excipient, the like or combinations thereof as listed in "Remington's Pharmaceutical Sciences," Mack Publishing Co., Easton, PA, 18th edition, 1990. can be used with a composition described herein. The various materials listed herein, alone or in combination, can be incorporated into or used with the materials described in Remington's. Any suitable techniques, carriers, and excipients can be used, including those understood in the art; e.g., in Remington's Pharmaceutical Sciences, above.

In some embodiments, a pharmaceutical composition comprising one or more cancer peptide agents described herein can be formulated, for example, as a topical formulation. The topical formulation may include, for example, a formulation such as a gel formulation, a cream formulation, a lotion formulation, a paste formulation, an ointment formulation, an oil formulation, and a foam formulation. The composition further may include, for example, an absorption emollient.

In some embodiments, at least part of the affected area of a mammal (e.g., a melanoma or surface-exposed cancer) is contacted with a composition on a daily basis, on an as-needed basis, or on a regular interval such as twice daily, three times daily, every other day, etc. A composition comprising one or more cancer peptide agents can be administered for a period of time ranging from a single as needed administration to administration for 1 day to multiple years, or any value there between, (e.g., 1-90 days, 1-60 days, 1-30 days, etc.). The dosages described herein can be daily dosages or the dosage of an individual administration, for example, even if multiple administrations occur (e.g., 2 sprays into a nostril).

Some embodiments relate to methods of treating or preventing cancer through administration of compositions comprising one or more cancer peptide agents described herein to the upper respiratory track/bronchi in a mammal in need thereof, for example, by contacting at least part of the upper respiratory tract/bronchi of a mammal with a therapeutically effective amount of a composition as disclosed above or elsewhere herein. The composition can be, for example, formulated as an aerosol formulation, including formulated for use in a nebulizer or an inhaler. The compositions may include, for example, one or more of dichlorodifluoromethane, trichlorofluoromethane, dichlorotetrafluoroethane, carbon dioxide, and the like. The pharmaceutical compositions can be formulated for use in a nebulizer or an inhaler, for example.

A pharmaceutical composition may comprise one or more suitable carriers. In some embodiments, a carrier includes one or more chemical compounds that facilitate the incorporation of an active ingredient (e.g., one or more cancer peptide agents) into cells or tissues. For example dimethyl sulfoxide (DMSO) is a commonly utilized carrier as it facilitates the uptake of many compounds and peptides into the cells or tissues of an organism. In some embodiments, a pharmaceutical carrier for a composition described herein can be selected from castor oil, ethylene glycol, monobutyl ether, diethylene glycol monoethyl ether, corn oil, dimethyl sulfoxide, ethylene glycol, isopropanol, soybean oil, glycerin, zinc oxide, titanium dioxide, glycerin, butylene glycol, cetyl alcohol, and sodium hyaluronate.

In certain embodiments, a pharmaceutical composition comprises hydrophobic excipients, additives, or other hydrophobic components. A pharmaceutical carrier for certain hydrophobic peptides can be a co-solvent system comprising benzyl alcohol, a nonpolar surfactant, a water-miscible organic polymer, and an aqueous phase. A common co-solvent system contemplated for use herein is the VPD co-solvent system, which is a solution of 3% w/v benzyl alcohol, 8% w/v of the nonpolar surfactant POLYSORBATE 80™, and 65% w/v polyethylene glycol 300, made up to volume in absolute ethanol. Naturally, the proportions of a co-solvent system can be varied considerably without destroying its solubility and toxicity characteristics. Furthermore, the identity of the co-solvent components can be varied: for example, other low-toxicity nonpolar surfactants can be used instead of POLYSORBATE 80™; the fraction size of polyethylene glycol can be varied; other biocompatible polymers can replace polyethylene glycol, e.g., polyvinyl pyrrolidone; and other sugars or polysaccharides can substitute for dextrose.

Alternatively or additionally, other carriers can be employed, if required. Liposomes and emulsions are well known examples of delivery vehicles or carriers for hydrophobic drugs and drug compositions. Additionally, the one or more cancer peptide agents described herein can be delivered using a sustained-release system, such as semipermeable matrices of solid hydrophobic polymers containing the therapeutic agent. The pharmaceutical compositions described herein can be administered to a patient per se, or in pharmaceutical compositions where they are mixed with other active ingredients, as in combination therapy, or suitable carriers or excipient(s). The compounds and compositions can be formulated with salts or excipients, such as for example, sodium or meglumine. Techniques for formulation and administration of the one or more cancer peptide agents of the instant application can be found in "Remington's Pharmaceutical Sciences," Mack Publishing Co., Easton, PA, 18th edition, 1990.

Furthermore, the compounds and compositions used herein can be stable over an extended period of time, for example on the order of months or years. Compositions described herein, in some embodiments, may comprise a preservative. The preservative can comprise a quaternary ammonium compound, such as benzalkonium chloride, benzoxonium chloride, benzethonium chloride, cetrimide, sepazonium chloride, cetylpyridinium chloride, or domiphen bromide (BRADOSOL®). The preservative can comprise an alkyl-mercury salt of thiosalicylic acid, such as thiomersal, phenylmercuric nitrate, phenylmercuric acetate or phenylmercuric borate. The preservative can comprise parabens, such as methylparaben or propylparaben. The preservative can comprise an alcohol, such as chlorobutanol, benzyl alcohol or phenyl ethyl alcohol. The preservative can comprise a biguanide derivative, such as chlorohexidine or polyhexamethylene biguanide. The preservative can comprise sodium perborate, imidazolidinyl urea, and/or sorbic acid. The preservative can comprise stabilized oxychloro complexes, such as known and commercially available under the trade name PURITE®). The preservative can comprise polyglycol-polyamine condensation resins, such as known and commercially available under the trade name POLYQUART® from Henkel KGaA. The preservative can comprise stabilized hydrogen peroxide generated from a source of hydrogen peroxide for providing an effective trace amount of resultant hydrogen peroxide, such as sodium perborate tetrahydrate. The preservative can be benzalkonium chloride.

The preservative can enable a composition to be used on multiple occasions. The preservative can reduce the effects of one or more of acid exposure, base exposure, air exposure, heat, and light on the active ingredient. The compounds and pharmaceutical compositions described herein can include any suitable buffers, such as for example, sodium citrate buffer and/or sequestering agents, such as edetate disodium sequestering agent. Ingredients, such as meglumine, may be added to adjust the pH of a composition or compound described herein. Compounds and compositions described herein may comprise sodium and/or iodine, such as organically bound iodine. Compositions and compounds used herein may be provided in a container in which the air is replaced by another substance, such as nitrogen.

Certain embodiments provide pharmaceutical compositions comprising one or more cancer peptide agents in an amount effective to achieve its intended purpose (e.g., a therapeutically effective amount). A "therapeutically effective amount" means an amount to prevent, treat, suppress, inhibit, reduce the severity of, delay the onset of, suppress or inhibit the growth or viability of a cancer, metastasis of a cancer or one or more symptoms associate with a cancer. A symptom can be a symptom already occurring or expected to occur. Determination of a therapeutically effective amount is well within the capability of those skilled in the art (e.g., a medical practitioner), especially in light of the detailed disclosure provided herein.

In some embodiments, a therapeutically effective amount is an amount needed for a significant quantity of a pharmaceutical composition (or cancer peptide agent therein) to contact a desired region or tissue where prevention or treatment of a cancer is desired.

The resulting effect of a treatment herein, in certain embodiments, is to provide a delay in the onset of metastasis or malignancy of a cancer, to inhibit, suppress or eliminate metastasis or malignancy of a cancer, to inhibit growth or viability of a cancer, to reduce the frequency or severity of symptoms associated with a cancer, to ameliorate symptoms associated with a cancer, to improve patient comfort or function, to decrease, reduce or inhibit the re-occurrence of a given cancer in a subject, to decrease the size of a tumor or cancer, to decrease the amount of cancer cells in a subject, to decrease the severity of a condition associated with a cancer, or to eliminate a cancer. The overall beneficial effect of a treatment described herein can be determined by comparing the condition or disease state of a subject who received a treatment described herein to one or more individuals who have not received treatment, or to the same patient prior to treatment, or after cessation of, treatment. A treatment may be complete (no detectable symptoms or cancer) or partial, such that fewer symptoms or amounts of a cancer are observed than would likely occur absent treatment.

Compositions described herein can be administered at a suitable dose, e.g., at a suitable volume and concentration depending on the route of administration. Within certain embodiments of the invention, dosages of an administered composition, one or more cancer peptide agents or peptide can be from a concentration, for example, of 0.1 ng/kg to 100 mg/kg (e.g., amount of active ingredient/body weight of a subject), 0.1 ng/kg to 1 mg/kg, 0.1 ng/kg to 100 µg/kg, 0.001 mg/kg to 100 mg/kg, 0.001 mg/kg to 10 mg/kg, 0.001 mg/kg to 1 mg/kg, about 0.01 mg/kg to 100 mg/kg, or about 0.01 mg/kg to about 50 mg/kg. In certain embodiments a composition or one or more cancer peptide agents described herein can be administered at a concentration of at least 0.01 mg/kg, at least 0.1 mg/kg, at least 1 mg/kg, at least 10 mg/kg, or at least 50 mg/kg. An active ingredient refers to a cancer peptide agent or a mixture of two or more cancer peptide agents. The concentrations recited above can refer to the concentration of a single cancer peptide agent, the collective concentration of a mixture of cancer peptide agents, or the concentration of each of two or more cancer peptide agents (e.g., peptides in a pharmaceutical composition or mixture). In certain embodiments a composition or one or more cancer peptide agents is administered to a concentration in a range of 0.1 mg/kg to 10 mg/kg body weight of a subject. Volumes suitable for intravenous administration are well known. For example, 0.1 ml-100 ml of a composition, one or more cancer peptide agents or peptide can be safely administered intravenously to an adult human subject.

Kits

In some embodiments the compositions, formulations, combination products and materials described herein can be included as part of kits, which kits can include one or more of the compositions, or cancer peptide agents described herein, formulations of the same, chemotherapeutic agents for combination treatments and products and other materials described herein. In some embodiments the kit comprises one or more a cancer peptide agents, or a pharmaceutical composition comprising the same. In some embodiments a kit comprises one or more cancer peptide agents as described herein and a chemotherapeutic agent. In some embodiments the products, compositions, kits, formulations, etc. can come in an amount, package, product format with enough medication (e.g., one or more cancer peptide agents) to treat a patient for 1 day to 1 year, 1 day to 180 days, 1 day to 120 days, 1 day to 90 days, 1 day to 60 days, 1 day to 30 days, or any day or number of days there between.

In some embodiments, a kit comprises suitable packaging materials. A kit optionally includes a label or packaging insert including a description of the components or instructions for use in vitro, in vivo, or ex vivo, of the components therein. Exemplary instructions include instructions for a method, treatment protocol or therapeutic regimen described herein. Labels or inserts include "printed matter," e.g., paper or cardboard, or separate or affixed to a component, a kit or packing material (e.g., a box), or attached to an ampule, tube or vial containing a kit component. Labels or inserts can additionally include a computer readable medium, optical disk such as CD- or DVD-ROM/RAM, DVD, MP3, magnetic tape, or an electrical storage media such as RAM and ROM or hybrids of these such as magnetic/optical storage media, FLASH media or memory type cards. Labels or inserts can include identifying information of one or more components therein, dose amounts, clinical pharmacology of the active ingredient(s) including mechanism of action, pharmacokinetics (PK) and pharmacodynamics (PD). Labels or inserts can include information identifying manufacturer information, lot numbers, manufacturer location and date.

Labels or inserts can include information on a condition, cancer, disorder, disease or symptom for which a kit component may be used. Labels or inserts can include instructions for the clinician or for a subject for using one or more of the kit components in a method, treatment protocol or therapeutic regimen. Instructions can include dosage amounts, frequency or duration, and instructions for practicing any of the methods, treatment protocols or therapeutic regimes set forth herein. Kits of the invention therefore can additionally include labels or instructions for practicing any of the methods and uses of the invention described herein.

Labels or inserts can include information on any benefit that a component may provide, such as a prophylactic or therapeutic benefit. Labels or inserts can include information on potential adverse side effects, such as warnings to the subject or clinician regarding situations where it would not be appropriate to use a particular composition. Adverse side effects could also occur when the subject has, will be or is currently taking one or more other medications that may be incompatible with the composition, or the subject has, will be or is currently undergoing another treatment protocol or therapeutic regimen which would be incompatible with the composition and, therefore, instructions could include information regarding such incompatibilities.

The term "packaging material" refers to a physical structure housing the components of the kit. The packaging material can maintain the components sterilely, and can be made of material commonly used for such purposes (e.g., paper, corrugated fiber, glass, plastic, foil, ampules, vials, tubes, etc.).

Components of the kit can be enclosed within an individual container and all of the various containers can be within a single package. Invention kits can be designed for cold storage.

The invention has been described herein using specific embodiments for the purposes of illustration only. It will be readily apparent to one of ordinary skill in the art, however, that the principles of the invention can be embodied in other ways. Therefore, the invention should not be regarded as being limited in scope to the specific embodiments disclosed.

EXAMPLES

Example 1

Network Approach for Identifying Cancer Peptide Agents

Shared amino acid sequence motifs among CMAPs were identified and used to develop novel peptides for the treatment of cancer. Cytoscape was used as a visualization platform to determine network topology. Cytoscape is an open-source software for integrating biomolecular interaction networks. Cytoscape's software core provides basic functionality to layout and query Protein-Peptide Network (PPN) arrangements; to visually integrate the network with expression profiles, phenotypes, and other molecular states; and to link the network to databases of functional annotations. To compute the topological parameters of both PPN and Sequence-Sharing Network (SSN) superimposed on PPN, we used the NetworkAnalyzer 2.0 [Via the internet at med.bioinf.mpi-inf. mpg.de/netanalyzer/], accessed online June 2017). NetworkAnalyzer 2.0 is a Java plugin for Cytoscape' the plugin helps compute many parameters describing an undirected network topology, which includes between-ness and centrality, collectively referred to as network statistics. Certain motifs of about 10 amino acids were detected by sequence alignment among networked CMAPs, which motifs manifest very low E-values compared with slightly modified sequence variations, indicating that they were not likely to have evolved by chance. An E value is a way to determine whether a particular amino acid sequence is very likely or very unlikely to have arisen by chance during evolution. The technique is a variation of BLAST (Basic Local Alignment Search Tool). The sequence E-value for each SSN generated set was BLASTed against the NCBI non-redundant protein sequences database.

Example 2

Treatment of Mice with a Cancer Peptide Agent

Experiments were performed to demonstrate that a cancer peptide agent arrested the process of metastasis. C57BL/6 mice were injected with 200,000 B16F10 or 500,000 mouse melanoma cells. Mice were treated daily with i.v. injections of the cancer peptide agent IR5-01 at 100 µg per injection, IR5-01 at 200 µg per injection, DMSO as a control or mice were not treated. On the $22^{nd}$ day (3 weeks, for 500 k injections) or $28^{th}$ day (4 weeks, for 200 k injections) after the tumor inoculation at least 10 mice from each group were sacrificed and their lungs were excised out, weighed, and placed in phosphate-buffered saline (PBS, pH 7.4). The number of the lung tumor nodules on the surface of the lung was counted and the percentage inhibition of lung tumor nodule formation was calculated. Results from representative experiments are shown in FIGS. 4 through 10.

Example 3

Sequences

```
                                        (SEQ ID NO: 1)
DVWSXGXXXY, where X can be any amino acid.

(SEQ ID NO: 2)
DXWSXGCXXY, where X can be any amino acid.

(SEQ ID NO: 3)
DXWSXGXXLY, where X can be any amino acid.

(SEQ ID NO: 4)
KSDXWSLGCXLY, where X can be any amino acid.

(SEQ ID NO: 5)
D(I/V)WS(L/M/I)G(C/I)(L/I)(L/M)Y (SEQ ID NO: 6, IR13-01)
DVWSLGCILY
```

-continued

```
                              (SEQ ID NO: 7, IR13-02)
DVWSIGCIMY (SEQ ID NO: 8, IR5-02)
DVWSMGILLY (SEQ ID NO: 9, IR5-01)
DIWSLGCLLY (SEQ ID NO: 10)
KSDVWSLGCILY (SEQ ID NO: 11)
KSKISPKSDVWSLGCILYYMT (SEQ ID NO: 12)
DVWSIGCIMYTLLVGKPPFET (SEQ ID NO: 13)
GKYDVPKWLSPSSILLLQQML (SEQ ID NO: 14)
DVWSLGCLLY (SEQ ID NO: 15)
NEKSDIWSLGCLLYELCALMP (SEQ ID NO: 16)
DX₁WSX₂GX₃X₄X₅Y, where X₁ and X₄ is selected
from I, V, and L, X₂ and X₅ is selected from
I, V, L and M, and X₃ is selected from C, I,
V, or L.
```

Example 4

Selected References

Liotta L A, Stetler-Stevenson W G: *Principles of Molecular Cell Biology of Cancer: Cancer Metastasis*. 4th edition. Philadelphia, PA: JB Lippincott Co.; (1993).

Barabasi A L and Oltvai Z N (2004) "Network biology: understanding the cell's functional organization" Nat Rev Genet 5:101.

Estrada E (2006) "Virtual identification of essential proteins within the protein interaction network of yeast" Proteomics 6:35-40.

Fabian M A (2005) "A small molecule-kinase interaction map for clinical kinase inhibitors" Nat Biotechnol 23:329.

Franz S (2005) "Drug discovery: playing dirty" Nature 437:942.

Gribbon P and Sewing A (2005) "High-throughput drug discovery: what can we expect from HTS?" Drug Discovery Today 10, 17.

Hampton T (2004) "Promiscuous anticancer drugs that hit multiple targets may thwart resistace" Jama 292, 419.

Hopkins A L (2007) "Network biology illuminates our understanding of drug action" Nat Biotechnology 25, 1110.

Ohlson S et al (1997) "Detection and characterization of weak affinity antibody antigen recognition with biomolecular interaction analysis" J Mol Recognit 10:135.

Ohlson S (2008) "Designing transient binding drugs: a new concept for drug discovery" Drug Discov Today 13:433.

Power C A (2003) "Knock out models to dissect chemokine receptor function in vivo" J Immunol Methods 273:73.

Roth B L et al 2004 "Magic shotguns versus magic bullets: selectively non-selective drugs for mood disorders and schizophrenia" Nat Rev Drug Discov 3, 353

Ruffner H et al (2007) "Human protein-protein interaction networks and the value for drug discovery" Drug Discovery Toda 12:709

Schwarz M K and Wells T N (2002) "New therapeutics that modulate chemokine networks" Nat Rev Drug Discov 1:347.

Vasilescu J and Figeys D (2006) "Mapping protein-protein interactions by mass spectrometry" Curr Opin Biotechnol 17:394.

Wong D T and Bymaster F P (2002) "Dual serotonin and noradrenaline uptake inhibitor class of antidepressants potential for greater efficacy or just hype?" Prog Drug Res 58:169.

Altschul S F, Gish W, Miller W, Myers E W, Lipman D J. (1990) Basic local alignment search tool. J Mol Biol 215:403-10; PMID:2231712.

Karlin S, Altschul S F. (1990) Methods for assessing the statistical significance of molecular sequence features by using general scoring schemes. Proc Natl Acad Sci USA 87:2264-8; PM ID: 2315319.

Dembo A, Karlin S, Zeitouni O. (1994) Limit distribution of maximal non-aligned two-sequence segmental score. Ann Probab. 22:2022-39.

Shannon P, Markiel A, Ozier O, Baliga N S, Wang J T, Ramage D, et al. (2003) Cytoscape: a software environment for integrated models of biomolecular interaction networks. Genome Res. 13:2498-504; PMID:14597658.

Assenov Y, Ramírez F, Schelhorn S E, Lengauer T, Albrecht M. (2008) *Computing topological parameters of biological networks*. Bioinformatics 24:282-4; PMID:18006545.

Chambers A F, Groom A C, MacDonald I C. (2002) *Dissemination and growth of cancer cells in metastatic sites*. Nature Rev Cancer 2:563-572. [PubMed: 12154349]

Fidler I J. (2003) The pathogenesis of cancer metastasis: the 'seed and soil' hypothesis revisited. Nature. Rev. Cancer 3:453-458. [PubMed: 12778135]

The foregoing references are incorporated herein by reference in their entirety.

The entirety of each patent, patent application, publication or any other reference or document cited herein hereby is incorporated by reference. In case of conflict, the specification, including definitions, will control.

Citation of any patent, patent application, publication or any other document is not an admission that any of the foregoing is pertinent prior art, nor does it constitute any admission as to the contents or date of these publications or documents.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described herein.

All of the features described herein may be combined in any combination. Each feature disclosed in the specification may be replaced by an alternative feature serving a same, equivalent, or similar purpose. Thus, unless expressly stated otherwise, disclosed features (e.g., antibodies) are an example of a genus of equivalent or similar features.

As used herein, all numerical values or numerical ranges include integers within such ranges and fractions of the values or the integers within ranges unless the context clearly indicates otherwise. Further, when a listing of values is described herein (e.g., about 50%, 60%, 70%, 80%, 85% or 86%) the listing includes all intermediate and fractional values thereof (e.g., 54%, 85.4%). Thus, to illustrate, reference to 80% or more identity, includes 81%, 82%, 83%, 84%, 85%, 86%, 87%, 88%, 89%, 90%, 91%, 92%, 93%, 94% etc., as well as 81.1%, 81.2%, 81.3%, 81.4%, 81.5%, etc., 82.1%, 82.2%, 82.3%, 82.4%, 82.5%, etc., and so forth.

Reference to an integer with more (greater) or less than includes any number greater or less than the reference number, respectively. Thus, for example, a reference to less than 100, includes 99, 98, 97, etc. all the way down to the number one (1); and less than 10, includes 9, 8, 7, etc. all the way down to the number one (1).

As used herein, all numerical values or ranges include fractions of the values and integers within such ranges and fractions of the integers within such ranges unless the context clearly indicates otherwise. Thus, to illustrate, reference to a numerical range, such as 1-10 includes 1, 2, 3, 4, 5, 6, 7, 8, 9, 10, as well as 1.1, 1.2, 1.3, 1.4, 1.5, etc., and so forth. Reference to a range of 1-50 therefore includes 1, 2, 3, 4, 5, 6, 7, 8, 9, 10, 11, 12, 13, 14, 15, 16, 17, 18, 19, 20, etc., up to and including 50, as well as 1.1, 1.2, 1.3, 1.4, 1.5, etc., 2.1, 2.2, 2.3, 2.4, 2.5, etc., and so forth.

Reference to a series of ranges includes ranges which combine the values of the boundaries of different ranges within the series. Thus, to illustrate reference to a series of ranges, for example, of 1-10, 10-20, 20-30, 30-40, 40-50, 50-60, 60-75, 75-100, 100-150, 150-200, 200-250, 250-300, 300-400, 400-500, 500-750, 750-1,000, 1,000-1,500, 1,500-2,000, 2,000-2,500, 2,500-3,000, 3,000-3,500, 3,500-4,000, 4,000-4,500, 4,500-5,000, 5,500-6,000, 6,000-7,000, 7,000-8,000, or 8,000-9,000, includes ranges of 10-50, 50-100, 100-1,000, 1,000-3,000, 2,000-4,000, etc.

Modifications can be made to the foregoing without departing from the basic aspects of the technology. Although the technology has been described in substantial detail with reference to one or more specific embodiments, those of ordinary skill in the art will recognize that changes can be made to the embodiments specifically disclosed in this application, yet these modifications and improvements are within the scope and spirit of the technology.

The invention is generally described herein using affirmative language to describe the numerous embodiments and aspects. The invention also specifically includes embodiments in which particular subject matter is excluded, in full or in part, such as substances or materials, method steps and conditions, protocols, or procedures. For example, in certain embodiments or aspects of the invention, materials and/or method steps are excluded. Thus, even though the invention is generally not expressed herein in terms of what the invention does not include aspects that are not expressly excluded in the invention are nevertheless described herein.

The technology illustratively described herein suitably can be practiced in the absence of any element(s) not specifically described herein. Thus, for example, in each instance herein any of the terms "comprising," "consisting essentially of," and "consisting of" can be replaced with either of the other two terms. The terms and expressions which have been employed are used as terms of description and not of limitation, and use of such terms and expressions do not exclude any equivalents of the features shown and described or segments thereof, and various modifications are possible within the scope of the technology claimed. The term "a" or "an" can refer to one of or a plurality of the elements it modifies (e.g., "a reagent" can mean one or more reagents) unless it is contextually clear either one of the elements or more than one of the elements is described. The term "about" as used herein refers to a value within 10% of the underlying parameter (i.e., plus or minus 10%), and use of the term "about" at the beginning of a string of values modifies each of the values (i.e., "about 1, 2 and 3" refers to about 1, about 2 and about 3). For example, a weight of "about 100 grams" can include weights between 90 grams and 110 grams. The term, "substantially" as used herein refers to a value modifier meaning "at least 95%", "at least 96%", "at least 97%", "at least 98%", or "at least 99%" and may include 100%. For example, a composition that is substantially free of X, may include less than 5%, less than 4%, less than 3%, less than 2%, or less than 1% of X, and/or X may be absent or undetectable in the composition.

Thus, it should be understood that although the present technology has been specifically disclosed by representative embodiments and optional features, modification and variation of the concepts herein disclosed can be resorted to by those skilled in the art, and such modifications and variations are considered within the scope of this technology.

What is claimed is:

1. A pharmaceutical composition comprising a cancer treating therapeutically effective amount of one or more cancer peptide agents consisting of an amino acid sequence selected from the group consisting of DVWSLGCILY (SEQ ID NO:6), DVWSIGCIMY (SEQ ID NO:7), DVWSMGILLY (SEQ ID NO:8), DIWSLGCLLY (SEQ ID NO:9), and DVWSLGCLLY (SEQ ID NO:14), and benzalkonium chloride.

2. The pharmaceutical composition of claim 1, wherein the one or more cancer peptide agents consists of the amino acid sequence of DIWSLGCLLY (SEQ ID NO:9).

3. The pharmaceutical composition of claim 1, wherein the pharmaceutical composition is formulated for injection, inhalation, ingestion or topical administration.

4. The pharmaceutical composition of claim 1, wherein the one or more cancer peptide agents consists of one cancer peptide agent consisting of the amino acid sequence of DVWSLGCILY (SEQ ID NO:6).

5. The pharmaceutical composition of claim 1, wherein the one or more cancer peptide agents consists of one cancer peptide agent consisting of the amino acid sequence of DVWSIGCIMY (SEQ ID NO:7).

6. The pharmaceutical composition of claim 1, wherein the one or more cancer peptide agents consists of one cancer peptide agent consisting of the amino acid sequence of DVWSMGILLY (SEQ ID NO:8).

7. The pharmaceutical composition of claim 1, wherein the one or more cancer peptide agents consists of one cancer peptide agent consisting of the amino acid sequence of DVWSLGCLLY (SEQ ID NO:14).

8. A method of treating cancer in a subject in need thereof comprising administering to the subject a therapeutically effective amount of a composition comprising one or more cancer peptide agents and benzalkonium chloride, wherein the one or more cancer peptide agents consists of an amino acid sequence selected from the group consisting of DVWSLGCILY (SEQ ID NO:6), DVWSIGCIMY (SEQ ID NO:7), DVWSMGILLY (SEQ ID NO:8), DIWSLGCLLY (SEQ ID NO:9), and DVWSLGCLLY (SEQ ID NO:14).

9. The method of claim 8, wherein the one or more cancer peptide agents consists of one cancer peptide agent consisting of the amino acid sequence of DIWSLGCLLY (SEQ ID NO:9).

10. A method of treating cancer in a subject in need thereof comprising administering a therapeutic amount of a composition comprising a cancer peptide agent consisting of the amino acid sequence of DIWSLGCLLY (SEQ ID NO:9).

11. The method of claim 8, wherein the subject is human.

12. The method of claim 8, wherein the cancer is selected from a carcinoma, adenocarcinoma, melanoma, neural neoplasia, sarcoma, lymphomas, myeloma, and leukemia.

13. The method of claim 8, wherein the method further comprises administering a chemotherapy or chemotherapeutic agent.

14. The method of claim 8, wherein the one or more cancer peptide agents consists of one cancer peptide agent consisting of the amino acid sequence of DVWSLGCILY (SEQ ID NO:6).

15. The method of claim 8, wherein the one or more cancer peptide agents consists of one cancer peptide agent consisting of the amino acid sequence of DVWSIGCIMY (SEQ ID NO:7).

16. The method of claim 8, wherein the one or more cancer peptide agents consists of one cancer peptide agent consisting of the amino acid sequence of DVWSMGILLY (SEQ ID NO:8).

17. The method of claim 8, wherein the one or more cancer peptide agents consists of one cancer peptide agent consisting of the amino acid sequence of DVWSLGCLLY (SEQ ID NO:14).

* * * * *